United States Patent
Linker et al.

(10) Patent No.: US 11,131,657 B2
(45) Date of Patent: Sep. 28, 2021

(54) METHOD AND SYSTEM FOR ESTIMATION OF FRUITLET DROP

(71) Applicant: TECHNION RESEARCH & DEVELOPMENT FOUNDATION LIMITED, Haifa (IL)

(72) Inventors: Raphael Linker, Misgav (IL); Boris Spektor, Haifa (IL); Yevgeniya Orlova, Kiryat Mozkin (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 16/933,479

(22) Filed: Jul. 20, 2020

(65) Prior Publication Data

US 2021/0018481 A1    Jan. 21, 2021

Related U.S. Application Data

(60) Provisional application No. 62/875,612, filed on Jul. 18, 2019.

(51) Int. Cl.

| | |
|---|---|
| *G01J 3/40* | (2006.01) |
| *G01N 33/02* | (2006.01) |
| *G01N 21/3563* | (2014.01) |
| *G01J 3/42* | (2006.01) |
| *G01N 21/84* | (2006.01) |
| *G01J 3/02* | (2006.01) |

(52) U.S. Cl.
CPC ............ *G01N 33/025* (2013.01); *G01J 3/027* (2013.01); *G01J 3/42* (2013.01); *G01N 21/3563* (2013.01); *G01N 21/84* (2013.01); *G01N 2021/8466* (2013.01)

(58) Field of Classification Search
CPC ........ G01J 3/28; G01J 3/40; G01J 3/02; G01J 3/08; G01J 3/42
USPC .......................................................... 356/303
See application file for complete search history.

(56) References Cited

U.S. PATENT DOCUMENTS

| | | | |
|---|---|---|---|
| 2016/0334276 A1* | 11/2016 | Pluvinage | G01J 3/28 |
| 2018/0181789 A1* | 6/2018 | Metzler | G06K 9/66 |

OTHER PUBLICATIONS

S. J. Wertheim, "Developments in the chemical thinning of apple and pear", Plant Growth Regulation, vol. 31 Issue 1-2 pp. 85-100, 2000.

(Continued)

*Primary Examiner* — Md M Rahman
(74) *Attorney, Agent, or Firm* — The Roy Gross Law Firm, LLC; Roy Gross

(57) ABSTRACT

A system comprising: at least one hardware processor; and a non-transitory computer-readable storage medium having stored thereon program instructions, the program instructions executable by the at least one hardware processor to: receive spectral data acquired from a plurality of fruits, wherein the spectral data is obtained within a specified range of wavelengths, at a training stage, train a machine learning model on a training set comprising: (i) the spectral data, and (ii) labels indicating, with respect to each of the fruits, a drop status within a specified time period subsequent to the acquiring, and at an inference stage, apply the machine learning model to target spectral data acquired from a target fruit, to predict the drop status of the target fruit within a specified time range subsequent to the acquiring.

20 Claims, 29 Drawing Sheets

(56) References Cited

OTHER PUBLICATIONS

Jure Kolaric, "Abscission of young apple fruits (*Malus domestica-Borkh.*): a review", Agricultura, vol. 7 pp. 31-36, 2010.

T. Webster, "Current approved thinning strategies for apples and pears and recent thinning research trials in Europe", The compact fruit tree, vol. 35 Issue 3 pp. 73-76,2002.

Carolina A. Torres et al., "Spectral fingerprints during sun injury development on the tree in Granny Smith apples: A potential non-destructive prediction tool during the growing season", Scientia Horticulturae, vol. 209, pp. 165-172, Jul. 2016.

Jean-Michel Roger et al. "EPO-PLS external parameter orthogonalisation of PLS application to temperature-independent measurement of sugar content of intact fruits", Chemometrics and Intelligent Laboratory Systems, vol. 66 Issue 2 pp. 191-204, 2003.

O. Safren et al., "Detection of green apples in hyperspectral images of apple-tree foliage using machine vision", Transactions of the ASABE, vol. 50 Issue 6 pp. 2303-2313, Nov. 2007.

Raphael A. Stern, "The photosynthesis inhibitor metamitron is a highly effective thinner for 'Golden Delicious' apple in a warm climate", Fruits, vol. 70 Issue 3 pp. 127-134, 2015.

Aman Ullah Malik and Zora Singh, "Improved fruit retention, yield and fruit quality in mango with exogenous application of polyamines", Scientia Horticulturae, vol. 110 Issue 2 pp. 167-174, 2006.

Sirinnapa Saranwong et al., "On-tree evaluation of harvesting quality of mango fruit using a hand-held NIR instrument", Journal of near infrared spectroscopy, vol. 11 Issue 4 pp. 283-294, 2003.

T.L. Robinson et al., "Advances in predicting chemical thinner response of apple using a carbon balance model", New York Fruit Quarterly, vol. 19 Issue 1 pp. 15-20, 2011.

Guglielmo Costa et al., "Use of Vis/NIR spectroscopy to assess fruit ripening stage and improve management in post-harvest chain", Fresh Produce, vol. 1 pp. 35-41, 2009.

Dias, P. A. et al. "Apple flower detection using deep convolutional networks", Computers in Industry, 99, 17-28., 2018.

Feng, J. et al., "Assessment of yellow-fleshed kiwifruit (*actinidia chinensis* 'hort16a') quality in pre-and post-harvest conditions using a portable near-infared spectrometer" HortScience, 46(1), 57-63. 2011.

Lakso, A. N. and Goffinet M. C., "Apple Fruit Growth", NY Fruit Quarterly 21(11), 11-14, 2013.

Linker, R. "Machine learning based analysis of night-time images for yield prediction in apple orchard", Biosystems Engineering, 167, 114-125, 2018.

Luo, X. et al. "Wavelength selection in vis/NIR spectra for detection of bruises on apples by ROC analysis", Journal of Food Engineering, 109(3), 457-466, 2012.

Miller, S. S. et al. "Performance of mechanical thinners for bloom or green fruit thinning in peaches", HortScience, 46 (1), 43-51, 2011.

Ngugi, H. K. and Schupp, J. R. "Evaluation of the risk of spreading fire blight in apple orchards with a mechanical string blossom thinner", HortScience, 44(3), 862-865, 2009.

Nicholson, C. et al. "A review of the most cost effective and efficient methods of thinning tree fruit crops in order to improve fruit quality and identify approaches worthy of further development", Agriculture and Horticulture Development Board, ADAS, UK. 2014.

Nicolai, B. M. et al. "Nondestructive measurement of fruit and vegetable quality by means of NIR spectroscopy: A review", Postharvest biology and technology, 46(2), 99-118, 2007.

Sadar, N. et al. "Spectrophotometrically determined pigment contents of intact apple fruits and their relations with quality: a review", Žemdirbystē(Agriculture), 100(1), 105-111, 2013.

Wang, C. et al. "Detection and counting of immature green citrus fruit based on the Local Binary Patterns (LBP) feature using illumination-normalized images" Precision Agriculture, 19, 1062-1083, 2018.

Diwan P. Ariana et al: "Near-infared hyperspectral reflectance imaging for detection of bruises on pickling cucumbers" Computers and Electronics in Agriculture 53 (2006) 60-70.

Hočevar, M., Širok, B., Godeša, T., & Stopar, M. (2014). Flowering estimation in apple orchards by image analysis. Precision agriculture, 15(4), 466-478.

Anatoly Gitelson et al: "Derivation of canopy light absorption coefficient from reflectance spectra", Remote Sensing of Environment, 231 (2019) 111276.

Anatoly Gitelson et al: "Relationships between leaf chlorophyll content and spectral reflectance and algorithms for non-destructive chlorophyll assessment in higher plant leaves", Journal of Plant Physiology, 160.271-282 (2003).

Anatoly Gitelson et al: "Quantitative estimation of chlorophyll-u using reflectance spectra: experiments with autumn chestnut and maple leaves", J. Photochem. Photobiol. B: Bioi., 22 (1994) 247-252.

Mark N. Merzlyak et al: "Reflectance spectral features and non-destructive estimation of chlorophyll, carotenoid and anthocyanin content in apple fruit", Postharvest Biology and Technology 27 (2003) 197-211.

I Wayan Budiastra et al: "Optical Methods for Quality Evaluation of Fruits (Part 2)—Prediction of Individual Sugars and Malic Acid Concentrations of Apples and Mangoes by the Developed NIR Reflectance System", Journal of the Japanese society of agricultural machinery vol. 60, No. 3 (1998).

Mark N. Merzlyak et al: "Light-stress-induced pigment changes and evidence for anthocyanin photoprotection in apples", J. Photochem. Photobiol. B: Biol. 55 (2000) 155-163.

I Wayan Budiastra et al: "Optical Methods for Quality Evaluation of Fruits (Part 1)—Optical Properties of Selected Fruits Using the Kubelka-hunk Theory and Their Relationships with Fruit Maturity and Sugar Content", Journal of the Japanese society of agricultural machinery vol. 60, No. 2 (1998), 117-128.

Jianwei Qin et al: "Measurement of the optical properties of fruits and vegetables using spatially resolved hyperspectral diffuse reflectance imaging technique", Postharvest Biology and Technology 49 (2008) 355-365.

Yevgeniya Orlova: "Forecasting the potential of apple fruitlet drop by in-situ Vis-NIR spectroscopy", Computers and Electronics in Agriculture, 169 (2020) 105225.

Alexei Solovchenko: "Localization of Screening Pigments Within Plant Cells and Tissues", Photoprotection in Plants, Springer Series in Biophysics 14, Springer-Verlag Berlin Heidelberg (2010), 67-88.

Anatoly Gitelson et al: "Non-Destructive Assessment of Chlorophyll Carotenoid and Anthocyanin Content in Higher Plant Leaves: Principles and Algorithms", Remote Sensing for Agriculture and the Environment, (2004), 78-94.

Craig Brodersen et al: "Do changes in light direction affect absorption profiles in leaves?", Functional Plant Biology, 2010, 37, 403-412.

Daniel Sims et al: "Relationships between leaf pigment content and spectral reflectance across a wide range of species, leaf structures and developmental stages", Remote Sensing of Environment 81 (2002) 337-354.

Matej Stopar: "Photosynthesis Inhibition as a Tool for Apple Fruitlet Thinning", Proceedings of the 6th Conference "Innovation in Fruit Growing", Belgrade, 27-36 (2017).

Abbott, J. A.: "Quality measurement of fruits and vegetables", Postharvest Biology and Technology, 15(3), 207-225 (1999).

* cited by examiner

METHOD AND SYSTEM FOR ESTIMATION OF FRUITLET DROP

CROSS REFERENCE TO RELATED APPLICATIONS

This application claims the benefit of priority under 35 U.S.C. § 119(e) of U.S. Provisional patent application No. 62/875,612, filed on Jul. 18, 2019, the contents of which is incorporated by reference as if fully set forth herein in its entirety.

FIELD OF THE INVENTION

The present invention relates to spectral imaging.

BACKGROUND OF THE INVENTION

Some trees, such as apple trees (*Malus domestica* Borkh) tend to exhibit a biennial cycle: a heavy-flowering year with an excessive amount of low-quality fruits is followed by a year with scarce flowering and low fruit load. In order to avoid this, growers must thin trees, i.e., cause unwanted young fruit (fruitlet) to drop. Chemical thinning with plant bioregulators is currently the only viable solution in large commercial operations. However, most thinners are effective only in the first few weeks following bloom, and thinning efficiency depends on numerous factors and is difficult to predict. Accordingly, the ability to forecast the expected fruitlet drop after an initial thinner application would help perform corrections with subsequent applications.

SUMMARY OF THE INVENTION

The following embodiments and aspects thereof are described and illustrated in conjunction with systems, tools and methods which are meant to be exemplary and illustrative, not limiting in scope.

There is provided, in an embodiment, a system comprising at least one hardware processor; and a non-transitory computer-readable storage medium having stored thereon program instructions, the program instructions executable by the at least one hardware processor to: receive spectral data acquired from a plurality of fruits, wherein the spectral data is obtained within a specified range of wavelengths, at a training stage, train a machine learning model on a training set comprising: (i) the spectral data, and (ii) labels indicating, with respect to each of the fruits, a drop status within a specified time period subsequent to the acquiring, and at an inference stage, apply the machine learning model to target spectral data acquired from a target fruit, to predict the drop status of the target fruit within a specified time range subsequent to the acquiring.

There is also provided, in an embodiment, a method comprising: receiving spectral data acquired from a plurality of fruits, wherein the spectral data is obtained within a specified range of wavelengths; at a training stage, training a machine learning model on a training set comprising: (i) the spectral data, and (ii) labels indicating, with respect to each of the fruits, a drop status within a specified time period subsequent to the acquiring; and at an inference stage, apply the machine learning model to target spectral data acquired from a target fruit, to predict the drop status of the target fruit within a specified time range subsequent to the acquiring.

There is further provided, in an embodiment, a computer program product comprising a non-transitory computer-readable storage medium having program instructions embodied therewith, the program instructions executable by at least one hardware processor to receive spectral data acquired from a plurality of fruits, wherein the spectral data is obtained within a specified range of wavelengths, at a training stage, train a machine learning model on a training set comprising: (i) the spectral data, and (ii) labels indicating, with respect to each of the fruits, a drop status within a specified time period subsequent to the acquiring, and at an inference stage, apply the machine learning model to target spectral data acquired from a target fruit, to predict the drop status of the target fruit within a specified time range subsequent to the acquiring.

In some embodiments, each of the fruits is a fruitlet.

In some embodiments, the specified range of wavelengths is from 400 nm to 1000 nm.

In some embodiments, the spectral data comprises at least one of spectral reflectance data and spectral fluorescence data.

In some embodiments, the spectral data comprises spectral data in one or more specified wavelengths within the specified range of wavelengths.

In some embodiments the spectral data comprises at least one of: a difference between a pair of specified wavelengths within the specified range of wavelengths, and a ratio between a pair of specified wavelengths within the specified range of wavelengths.

In some embodiments, the acquiring comprises acquiring at least some of the spectral data between 4-16 days after treatment (DAT) of the fruits and the target fruit with a thinning agent.

In some embodiments, the specified time period is between 20-30 DAT of the fruits and the target fruit with a thinning agent.

In some embodiments, the receiving further comprises performing a dimensionality reduction step with respect to the spectral data.

In some embodiments, the receiving further comprises correcting the spectral data for sunlight contribution during the acquiring.

In some embodiments, the receiving further comprises correcting for temperature differences in the fruits during the acquiring.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 5A-10B show experimental results, in accordance with some embodiments of the present disclosure;

FIGS. 13-19B show experimental results, in accordance with some embodiments of the present disclosure.

DETAILED DESCRIPTION OF THE INVENTION

Figure 1A:
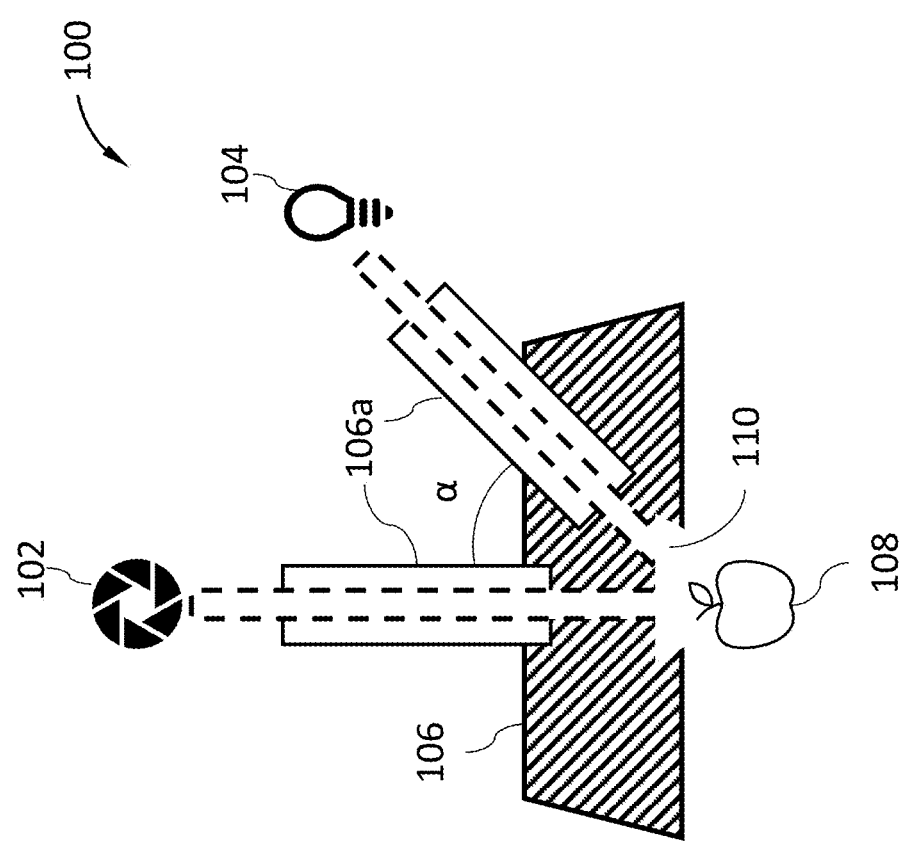
FIG. 1A-1C schematically illustrate exemplary system 100 for predicting an expected fruitlet drop rate in fruit trees, based, at least in part, on in-situ spectral imaging, in accordance with some embodiments of the present disclosure.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, us of the conjunction "or" as used herein is to be understood as inclusive (any or all of the stated options).

Disclosed herein are a system, method, and computer program product for predicting fruitlet drop rate in fruit trees, based, at least in part, on in-situ spectral imaging of fruitlets.

In some embodiments, the present disclosure provides for in-situ spectroscopy of fruitlets in a tree, in the visible and near-infrared (Vis-NIR) ranges, to predict fruitlet drop. In some embodiments, the present disclosure measure reflectance over the 400-1000 nm range.

In some embodiments, the tree may be treated with a thinning agent, and the in-situ spectroscopy may be performed within a specified number of days after treatment (DAT), e.g. between 4-12 DAT. In some embodiments, these measurements may be used to forecast fruitlet drop by 20-26 DAT. In some embodiments, the timing of treatment, in-situ spectroscopy, and forecast may be shifted, e.g., in colder climates where fruitlet growth may be delayed by several days. Accordingly, in some embodiments, depending on climate, the in-situ spectroscopy may be performed, e.g., within 4-16 DAT, and may be used to forecast fruitlet drop by 20-30 DAT. In some embodiments, different DAT ranges may be used in different geographical regions, based on differences in regional and/or seasonal climate and their effect on fruitlet growth timeline.

In some embodiments, the present disclosure provides for controlling for sunlight contribution parameter in the collected measurement during the in situ measurement, to correct any sunlight contribution in a data preprocessing stage.

In some embodiments, the present disclosure provides for training a machine learning model on spectral reflectance data collected from a plurality of fruitlets in situ. In some embodiments, a trained machine learning model of the present disclosure may provide for predicting, at an inference stage, a likelihood of a target fruitlet drop based on target reflectance data acquired from the target fruitlet.

Without external intervention, apple trees tend to exhibit a biennial cycle, where an abundance of flowers/fruitlets in one year is followed by scarce flowering in a subsequent year. Heavy-flowering, and therefore high fruit load, on a tree results in small, poorly colored, low-quality fruit. These further inhibit bud initiation for the subsequent year causing low fruit load, very large fruit size, and high fruit susceptibility to physiological disorders.

The biennial bearing cycle may persist with great regularity as under normal conditions the natural thinning process, known as "June drop," is insufficient to remove the excess of young fruits (fruitlets). Therefore, in commercial apple orchards, additional thinning is performed by the grower to achieve a stable production, both in terms of fruit number and fruit size (quality). Such fruit removal can be achieved by either mechanical or chemical thinning with plant bioregulators at the beginning of the season, or by hand-thinning in mid-season.

Hand thinning is a labor-intensive and high-cost solution. Mechanical thinning has several disadvantages, including inconsistency in results, non-selectivity in flower/fruitlet removal (fruitlets at certain positions have higher survival potential) and increase in the risk of disease spread. On the other hand, it has been demonstrated that adequate chemical thinning improves fruit size and quality. Due to the prohibitive cost of hand thinning and the drawbacks of mechanical thinning, chemical thinning is currently the only viable solution in large commercial operations.

Unfortunately, the impact of chemical thinning depends on environmental conditions and tree status and the results are inconsistent from one season to the next. Thinner efficiency also depends on the time of application and most thinners are effective only before the fruitlet diameter reaches ~12 mm, which restricts their application window to a few weeks after bloom. Due to the relatively unpredictable impact of thinner application, growers tend to err on the side of caution by using multiple bioregulators applications to achieve the adequate thinning efficiency. Clearly, efficient management of repeated applications requires estimation of the fruitlet drop due to previous applications. However, due to the narrow time-window for applying thinner, decisions have to be made before the actual fruitlet drop, thus the expected fruitlet drop must be estimated. To date, there is no known measurement procedure that can provide this kind of information, which leaves growers to rely on experience and general guidelines.

Accordingly, in some embodiments, the present disclosure provides for a measurement technique produces a reliable estimate of the expected drop rate of fruitlets based on measurements acquired within 9 to 17 days after bloom.

In some embodiments the present disclosure, uses spectral imaging in the visible and near-infrared (Vis-NIR) range. This technique is rapid, non-destructive, and suitable for in-situ measurements. Although Vis-NIR spectroscopy is often used to assess harvest and post-harvest fruit properties in controlled environments, implementation of the technique for on-tree assessment is much more challenging. Field measurements are greatly affected by sunlight and fruit temperature fluctuations. Furthermore, performing spectral measurements with respect to young fruit (fruitlets) also presents numerous challenges. Fruitlets contain a high amount of pigments, including chlorophyll and phenolic compounds, which are prone to quick oxidation. Consequently, detaching fruitlets and performing measurements under laboratory conditions involves addressing these issues, in addition to the method being destructive to the budding fruit.

Accordingly, in some embodiments the present disclosure provides for Vis-NIR spectroscopy in-situ as a tool for forecasting fruitlet drop rate.

In some embodiments, the method comprises: acquiring reflectance intensity (R) of a fruit at specified wavelength ranges across the electromagnetic spectrum, calculating a corrected reflectance index (CRI) for each fruit within a plurality of fruits with respect to the specified wavelength ranges; and identifying a fruit having a CRI value within a range of values indicative of an expected fruitlet drop.

In some embodiments, the method further comprises estimating a number of fruits identified as expected to drop in a tree. In some embodiments, estimating comprises counting the fruits identified as expected to drop. In some embodiments, estimating comprises using the estimate of the number of fruits identified as expected to drop and applying a statistical model to estimate a number of non-identified fruits, e.g., in the tree. In some embodiments, estimating comprises correcting the calculated number of fruits identified as expected to drop by applying a statistical model. In some embodiments, estimating comprises counting the identified fruits and adding non-identified fruits in accordance with the statistical model.

In another aspect, the method comprises predicting an expected drop rate in a tree, wherein the drop may be is induced by treating a plant with a chemical thinner or any other agent acting as abscission enhancers. In some embodiments, abscission is induced by administering a thinning agent to the plant. In some embodiments, administering a thinning agent induces abscission of at least a part of a plant. In some embodiments, administering a thinning agent to at least a part of the plant induces fruit drop.

In some embodiments, a thinning agent comprises any of, e.g., synthetic auxins (such as 1-naphthaleneacetic acid, as 1-naphthaleneacetamide) photosynthesis inhibitors (such as Metametron) and cytokinines (Benzyladenine).

In another aspect, the method comprises measuring reflectance of a fruit at a range of wavelengths. In some embodiments, the range is selected from visible and/or infrared spectral range. In some embodiments, the range is from 400 nm to 1000 nm, from 400 to 500 nm, from 600 to 700 nm, from 400 to 430 nm, from 650 to 680 nm, from 650 to 750 nm, from 800 to 1000 nm.

In some embodiments, the method comprises measuring reflectance of a fruit at a plurality of distinct wavelengths. In some embodiments, the plurality of distinct wavelengths is within visible and/or infrared spectral range. In some embodiments, the plurality of distinct wavelengths comprises at least two of (a) 973 nm±20 nm, (b) 404 nm±20 nm, (c) 674±20 nm, and (d) 693±20 nm.

In some embodiments, any of the plurality of distinct wavelengths is selected from a wavelength range. In some embodiments, the plurality of distinct wavelengths comprises at least two of (a), (b), (c), and (d). In some embodiments, the range of (a) is from 850 to 1000 nm, from 950 to 1000 nm, or any range and/or value therebetween. In some embodiments, the range of (b) is from 400 to 500 nm, from 400 to 450 nm, from 400 to 430 nm, from 450 to 500 nm, or any range and/or value therebetween. In some embodiments, the range of (c) and/or (d) is from 600 to 750 nm, from 650 to 700 nm, from 670 to 750 nm, from 680 to 720 nm, or any range and/or value therebetween.

In some embodiments, reflectance of a fruit is measured at two or more distinct wavelengths, wherein a first distinct wavelength is any of (a) and the second distinct wavelength is any of (b). In some embodiments, reflectance of a fruit is measured at two or more distinct wavelengths, wherein a first distinct wavelength is any of (c) and a second distinct wavelength is any of (d).

In another aspect, the method comprises calculating a corrected reflectance index (CRI) for each fruit within a plurality of fruits. In some embodiments, CRI is calculated by determining a difference between R(a) and R(b). In some embodiments, CRI is calculated by determining; a ratio of R(d) to R(c). In some embodiments, CRI is calculated by determining a difference between R(a) and R(b) and by determining a ratio of R(d) to R(c). R(a) to reflectance (d) are values of reflectance at corresponding wavelengths.

In some embodiments, CRI is calculated by determining a difference between R(a) and R(b) at a time range of less than 6 days after treatment (DAT) the plant with a thinning agent. In some embodiments, CRI is calculated by determining a difference between R(a) and R(b) at less than 5 DAT, less than 4 DAT, less than 3 DAT, less than 2 DAT.

In some embodiments, CRI is calculated by determining a ratio of R(d) to R(c) at a time range of more than 5 DAT. In some embodiments, CRI is calculated by determining a ratio of R(d) to R(c) at a time range of more than 6 DAT, of more than 7 DAT, of more than 8 DAT, of more than 10 DAT, of more than 15 DAT, of more than 20 DAT.

In some embodiments, CRI is calculated by determining a difference between R(a) and R(b) at a time range of less than 10 days after full bloom (DAFB). In some embodiments, CRI is calculated by determining a ratio of R(d) to R(c) at a time range of more than 10 DAFB. In some embodiments, different time ranges may be used in different geographical regions, based on differences in regional and/or seasonal climate and their effect on fruitlet growth timeline.

In another aspect, calculating CRI comprises correcting for a sunlight contribution. In some embodiments, sunlight contribution correction comprises subtracting a value of a background from the value of CRI. In some embodiments, sunlight contribution correction comprises subtracting a value of the background from any of R(a) to R(d) values. In some embodiments, a value of the background is calculated by acquiring reflectance of the non-illuminated fruit. The correction of sunlight contribution may be performed by positioning a shutter within a light pass of the system. Reflectance values are acquired at both opened and closed shutter position. In the opened shutter position, reflected light from the light source illumination was measured, together with the sunlight contribution. In the closed shutter position, the light source illumination was blocked, and only the background sunlight contribution was assessed.

In some embodiments, a light source of the present disclosure may comprise a LED-based device. In such cases, sunlight interference may be corrected using light modulation instead of a mechanical shutter, based on a similar principle.

In some embodiments, a validation of correction of sunlight contribution may be performed by acquiring a signal intensity at 764±10 nm, caused by molecular oxygen absorption in the atmosphere. If the signal intensity at 764±10 nm is above a predetermined threshold value, such measurement is discarded.

In some embodiments, calculating CRI comprises correcting for temperature differences.

In another aspect of the present invention, provided herein a method comprising: acquiring reflectance of a fruit at a wavelength parameter, thereby estimating a growth stage of the fruit; calculating CRI for the fruit according to any of: a difference between R(a) and R(b), and/or a ratio of R(d) to R(c) with respect to the growth stage of the fruit; and identifying a fruit within the plurality of fruits having a CRI value within a range of values indicative of the abscission of the fruit.

In another aspect, the method comprises estimating a growth stage of the fruit. In some embodiments, the growth stage is estimated by measuring reflectance value of the fruit. In some embodiments, the growth stage is estimated by calculating a hair density on a surface of the fruit. In some embodiments, reflectance value is related to a hair density on a surface of the fruit. In some embodiments, a reduced hair density on a surface is related to an advanced growth stage of the fruit. In some embodiments, an increased hair density on a surface is related to an earlier growth stage of the fruit. In some embodiments, the fruit destined to drop is characterized by a greater hair density. In some embodiments, the fruit destined to drop is characterized by increased light scattering, compared to an intact fruit.

In some embodiments, reflectance value is related to a chlorophyll content of the fruit and to a hair density on a surface of the fruit.

In some embodiments, the growth stage is estimated by calculating a chlorophyll content of the fruit. In some embodiments, chlorophyll content measurement is based on measuring reflectance, wherein reflectance may be correlated with a hair density on a surface of the fruit. In some embodiments, reflectance value is related to a chlorophyll content of the fruit. In some embodiments, a reduced chlorophyll content is related to an earlier growth stage of the fruit. In some embodiments, an increased chlorophyll content is related to an advanced growth stage of the fruit.

In some embodiments, reflectance value is related to a density of fruit compartment.

In another aspect, the range of values indicative of the abscission of the fruit is related to a difference in hair density between an intact fruit and a fruit identified as predicted to abscise. In some embodiments, the range of values indicative of the abscission of the fruit is related to a difference in chlorophyll content between an intact fruit and a fruit identified as predicted to abscise. In some embodiments, the range of values indicative of the abscission of the fruit is related to a difference in chlorophyll content and to a difference in hair density between an intact fruit and a fruit identified as predicted to abscise.

In some embodiments, CRI is calculated as described herein above. In some embodiments, CRI is calculated by any of: a difference between R(a) and R(b), and/or a ratio of R(d) to R(c) with respect to the growth stage of the fruit. In some embodiments, CRI is calculated by any of: a difference between R(a) and R(b), and/or a ratio of R(d) to R(c) with respect to the hair density, and/or chlorophyll content of the fruit.

In some embodiments, CRI is calculated by applying a difference between R(a) and R(b) at an earlier growth stage. In some embodiments, the earlier growth stage is less than 10 DAFB.

In some embodiments, CRI is calculated by applying a ratio of R(d) to R(c) at an advanced growth stage. In some embodiments, the advanced growth stage is more than 10 DAFB.

In some embodiments, the wavelength parameter is as defined hereinabove.

In some embodiments, the abscission is as defined hereinabove.

In another aspect, the method comprises estimating a number of fruits identified as predicted to abscise, as described hereinabove.

In some embodiments, identifying is as described hereinabove.

In another aspect of the present invention, provided herein a method, comprising: acquiring a fluorescence intensity (F) of a fruit at an emission wavelength parameter, wherein the emission wavelength parameter comprises a) one or more distinct emission wavelengths, and/or b) a range of emission wavelengths; calculating corrected fluorescence index (CFI) for the fruit with respect to the emission wavelength parameter; and identifying a fruit within a plurality of fruits having a CFI value within a range of values indicative of the abscission of the fruit.

In some embodiments, the method comprises estimating a number of fruits identified as predicted to abscise.

In some embodiments, the method comprises acquiring F of a fruit at any of: a) one or more distinct wavelengths, and/or b) a range of wavelengths, thereby estimating a chlorophyll content of the fruit. In some embodiments, value of F is predetermined by a chlorophyll content of the fruit and by hair density on the surface of the fruit. In some embodiments, the fruit destined to drop has a greater hair density, than the intact fruit. In some embodiments, the fruit destined to drop causes higher scattering of the excitated and emitted light from the fruits surface.

In another aspect, the emission wavelength parameter comprises a) one or more distinct emission wavelengths, and/or b) a range of emission wavelengths.

In some embodiments, any of one or more distinct emission wavelengths, and/or a range of emission wavelengths are in a range from 400 nm to 1200 nm, from 400 to 500 nm, from 600 to 700 nm, from 400 to 430 nm, from 650 to 680 nm, from 650 to 750 nm, from 800 to 1000 nm, from 100 to 1200 nm. In some embodiments the one or more emission wavelength is in the emission range of chlorophyll.

In another aspect, CFI is calculated with respect to the sunlight contribution correction.

In some embodiments, the abscission is as described hereinabove.

In some embodiments, identifying is as described hereinabove.

In another aspect, any of the methods of the invention comprising predicting an efficiency of the abscission agent.

In some embodiments, the method of the present invention comprises a method for crop estimation, such as immature fruit detection, and/or a fruit load, from a crop of plants located within a geographical region from image data of a plurality of scenes acquired in an image sensor. The scene may include, for example, pictures of fruit trees, or parts of fruit trees, planted in the geographical location, typically an orchard. The image sensors, typically a camera, for example, may be coupled to an image processing unit where the image data may be processed to identify fruits on a fruit tree in the captured image of the fruit tree in the scene, for example. Image processing and/or computer vision algorithms may be used to distinguish between green fruits (e.g., before ripening) and green leaves. Such methods for fruit detection in the captured image are known in the art and may be used for automatization of data sampling (e.g. measurement the intensity of reflectance and/or F from fruit).

In another aspect of the present invention, provided herein a system comprising: at least one light source configured to illuminate a fruit; a detector configured to acquire reflectance intensity (R) from the fruit illuminated by said light source at a wavelength parameter, wherein said wavelength parameter comprising: a plurality of distinct wavelengths, and/or a wavelength range; and a processor in communication with said sensor and configured to: calculate a corrected reflectance index (CRI) for each fruit within a plurality of fruits with respect to said wavelength parameter; identify a fruit within said plurality of fruits having a CRI value within a range of values indicative of the abscission of said fruit; and generate an output on an output device with information related to a number of fruits identified as predicted to abscise.

In another aspect of the present invention, provided herein a system comprising: at least one light source configured to illuminate a fruit; a detector configured to acquire reflectance intensity (R) from the fruit illuminated by said light source at a wavelength parameter, wherein said wavelength parameter comprising: a plurality of distinct wavelengths, and/or a wavelength range; and a processor in communication with said sensor and configured to: estimate a growth stage of the fruit; calculate a corrected reflectance index (CRI) for each fruit within a plurality of fruits with respect to the wavelength parameter; identify a fruit within said plurality of fruits having a CRI value within a range of values indicative of the abscission of said fruit; and generate an output on an output device with information related to a number of fruits identified as predicted to abscise.

In another aspect, a wavelength range is from 400 nm to 1000 nm. In some embodiments, the range is from 400 nm to 1000 nm, from 400 to 500 nm, from 600 to 700 nm, from 400 to 430 nm, from 650 to 680 nm, from 650 to 750 nm, from 800 to 1000 nm.

In some embodiments, a plurality of distinct wavelengths is within visible and/or infrared spectral range. In some embodiments, the plurality of distinct wavelengths comprises at least two of (a) 973 nm±20 nm, (b) 404 nm±20 nm, (c) 674±20 nm, and (d) 693±20 nm.

In some embodiments, any of the plurality of distinct wavelengths is selected from a wavelength range. In some embodiments, the plurality of distinct wavelengths comprises at least two of (a), (b), (c), and (d). In some embodiments, the range of (a) is from 850 to 1000 nm, from 950 to 1000 nm, or any range and/or value therebetween. In some embodiments, the range of (b) is from 400 to 500 nm, from 400 to 450 nm, from 400 to 430 nm, from 450 to 500 nm, or any range and/or value therebetween. In some embodiments, the range of (c) and/or (d) is from 600 to 750 nm, from 650 to 700 nm, from 670 to 750 nm, from 680 to 720 nm, or any range and/or value therebetween.

In another aspect, the system comprises at least one light source. A light source may be a sunlight or an artificial source of light emitting light at visible and/or infrared spectrum. For example, a halogen lamp, or a LED device can be used as a light source. In some embodiments, the light source comprises a sunlight and an artificial source of light. In some embodiments, the system comprises one or more artificial sources of light. In some embodiments, the system comprises a shutter positioned in the light pass. In some embodiments, the system comprises a light source in communication with a processor.

In another aspect, a light emitted from the light source is transferred to the fruit by an optical fiber. In some embodiments, the light from the light source illuminates the fruit. In some embodiments, the light source provides an illuminated light.

In another aspect, the system comprises a detector configured to acquire reflectance intensity (R) from the fruit. In some embodiments, the detector is configured to acquire reflectance at a wavelength range from 400 nm to 1000 nm. In some embodiments, the range is from 400 nm to 1000 nm, from 400 to 500 nm, from 600 to 700 nm, from 400 to 430 nm, from 650 to 680 nm, from 650 to 750 nm, from 800 to 100 nm.

In some embodiments, the detector is in communication with a processor. In some embodiments, the detector is a part of a spectrometer. In some embodiments, a reflected light from the fruit is transferred to the detector by an optical fiber.

In some embodiments, the detector may include a camera, such as a monochromatic camera. Such monochromatic cameras may include a plurality of photo-sites, or light sensors, arranged in a spatial array. Each light sensor may produce an electrical signal proportional to the light intensity or light power impinging on the active area of the light sensor for a given period of time (e.g., integration time). However, the monochromatic light sensors are typically sensitive to all visible and NIR wavelengths impinging on the active area of the light sensors. In some embodiments, filters may be used to differentiate between the at least two wavelengths.

In another aspect, the system comprises a processor in communication with the detector, wherein the processor is configured to estimate a growth stage of the fruit;
to calculate a corrected reflectance index (CRI) for each fruit within a plurality of fruits with respect to the wavelength parameter; to identify a fruit within the plurality of fruits having a CRI value within a range of values indicative of the abscission of the fruit; and generate an output on an output device with information related to a number of fruits identified as predicted to abscise.

In some embodiments, the processor is in communication with any of: one or more light source, one or more detectors, and with an additional device (e.g. a thermometer).

In some embodiments, the processor is coupled to a memory and a storage device. Processor may include one or more processing units, e.g. of one or more computers.

Processor may be configured to communicate with an input/output terminal including an input device and an output device via an input/output interface. Input/output terminal may include a computer.

Processor may be configured to communicate with an input device. For example, input device may include one or more of a keyboard, keypad, or pointing device for enabling a user to inputting data or instructions for operation of processor.

For example, an output device may include a computer monitor or screen. Processor may be configured to communicate with a screen of output device to output information related to the identified presence of fruits in image data of scenes of plants, such as fruit trees, with fruit. In another example, output device may include a printer, display panel, speaker, or another device capable of producing visible, audible, or tactile output.

Processor may be configured to communicate with memory. Processor may be configured to communicate with data storage device. Data storage device may include one or more fixed or removable nonvolatile data storage devices. For example, data storage device may include a computer readable medium for storing program instructions for operation of processor. In this example, the programmed instructions may take the form of image processing routines and/or instructions in a spectral processing module, a deep learning module, a statistical processing module, and a proximity processing module for processing the image data of scenes in the image sensors and/or detectors.

In some embodiments, the processor is configured to apply a statistical model, for estimating a number of not identified fruits. In some embodiments, the model provides a statistical correction for the number of fruits identified to drop.

In another aspect, the system comprises a thermometer. In some embodiments, the thermometer is in communication with the processor.

In another aspect, the system comprises a probe. In some embodiments, a probe comprising at least one of: an optical fiber, a housing, and a shutter comprising a hole. In some embodiments, the probe comprises two or more optical fibers. In some embodiments, the optical probe is in communication with the detector and/or the light source. In some embodiments, the detector and/or the light source are in communication with the probe via optical fibers.

In some embodiments, the probe comprises one or more detectors, and one or more light sources. In some embodiments, the one or more detectors, and the one or more light sources are positioned within the housing.

In some embodiments, the probe comprises a housing. In some embodiments, the housing comprises fiber holders for the two or more optical fibers. In some embodiments, the probe comprises a shutter comprising a hole.

In some embodiments, the probe comprises a first optical fiber connected to the detector. In some embodiments, the probe comprises a second optical fiber connected to the light source. In some embodiments, the probe comprises one or more optical fibers connected to the one or more light sources. In some embodiments, the probe comprises one or more optical fibers connected to the one or more detectors.

In another aspect, the first optical fiber and the second optical fiber are positioned at an angle ranging from 15 to 90° within the probe. In some embodiments, the first optical fiber and the second optical fiber are positioned at an angle ranging from 15 to 90° within the housing. In some embodiments, the first optical fiber and the second optical fiber are positioned at an angle of 45° within the housing.

In some embodiments, a distance from any of the first optical fiber and/or the second fiber to the shutter within said probe is from 10 to 100 mm.

In some embodiments, the hole has a conical configuration. In some embodiments, the hole acts as a collimator. In some embodiments, the illuminated light from the light source and/or reflected light from the fruit pass across the hole. In some embodiments, a diameter of the hole is from 0.1 to 10 mm, from 0.5 to 5 mm, from 1 to 3 mm.

In some embodiments, the shutter in close proximity to the fruit. In some embodiments, the shutter comprises a flexible material configured to prevent damage to the fruit.

In another aspect, the probe is configured to provide an illumination spot having a diameter from 1 to 10 mm, from 1 to 5 mm.

In another aspect of the invention, provided herein a system comprising: at least one light source configured to illuminate a fruit; a detector configured to acquire a fluorescence intensity (F) of a fruit illuminated by the light source at an emission wavelength parameter, wherein the emission wavelength parameter comprises a) a plurality of distinct wavelengths, and/or b) a range of wavelengths; calculating corrected fluorescence index (CFI) for the fruit with respect to the emission wavelength parameter; identifying a fruit within a plurality of fruits having a CFI value within a range of values indicative of the abscission of the fruit; and a processor in communication with the detector and configured to: estimate a chlorophyll content of the fruit; calculate CFI for each fruit within a plurality of fruits with respect to the emission wavelength parameter; identify a fruit within said plurality of fruits having a CFI value within a range of values indicative of the abscission of said fruit; and generate an output on an output device with information related to a number of fruits identified as predicted to abscise.

In some embodiments, the plurality of distinct emission wavelengths, and/or the range of emission wavelengths are in a range from 400 nm to 1200 nm, from 400 to 500 nm, from 600 to 700 nm, from 400 to 430 nm, from 650 to 680 nm, from 650 to 750 nm, from 800 to 1000 nm, from 100 to 1200 nm.

In another aspect, the system comprises at least one light source configured to illuminate a fruit at an excitation wavelength in a range from 400 nm to 1000 nm. In some embodiments the excitation wavelength is in the excitation range of chlorophyll.

In another aspect, the system comprises a detector configured to acquire F at a wavelength range from 400 nm to 1200 nm, from 400 to 500 nm, from 600 to 700 nm, from 400 to 430 nm, from 650 to 680 nm, from 650 to 750 nm, from 800 to 1000 nm, from 100 to 1200 nm. In some embodiments the emission wavelength is in the emission range of chlorophyll.

In some embodiments, the detector is in communication with a processor. In some embodiments, the detector is a part of a fluorimeter. In some embodiments, emitted light from the fruit is transferred to the detector by an optical fiber.

In another aspect, system comprises a probe, as described hereinabove. In some embodiments, the first optical fiber and the second optical fiber are positioned at an angle of 90° within the probe.

Different embodiments are disclosed herein. Features of certain embodiments may be combined with features of other embodiments; thus, certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

System

FIG. 1A schematically illustrates an exemplary system 100 for predicting an expected fruitlet drop rate in fruit trees, based, at least in part, on in-situ spectral imaging, in accordance with some embodiments of the present disclosure.

In some embodiments, system 100 comprises a spectral imaging device 102, e.g., a spectrometer, a light source 104, a fiber-optical holder 106 comprising fiber optic probes 106a, and an aperture 110 for acquiring reflectance from a sample, e.g., a fruitlet 108 in situ. System 100 may further comprise a processing module comprising one or more hardware processors and one or more computer-readable, non-transitory, storage mediums.

System 100 as described herein is only an exemplary embodiment of the present invention, and in practice may have more or fewer components than shown, may combine two or more of the components, or a may have a different configuration or arrangement of the components. The various components of system 100 may be implemented in hardware, software or a combination of both hardware and software. In various embodiments, system 100 may comprise a dedicated hardware device, or may form an addition to/or extension of an existing device. In some embodiments, system 100 may comprise numerous general purpose or special purpose computing system environments or configurations.

Figure 1B:
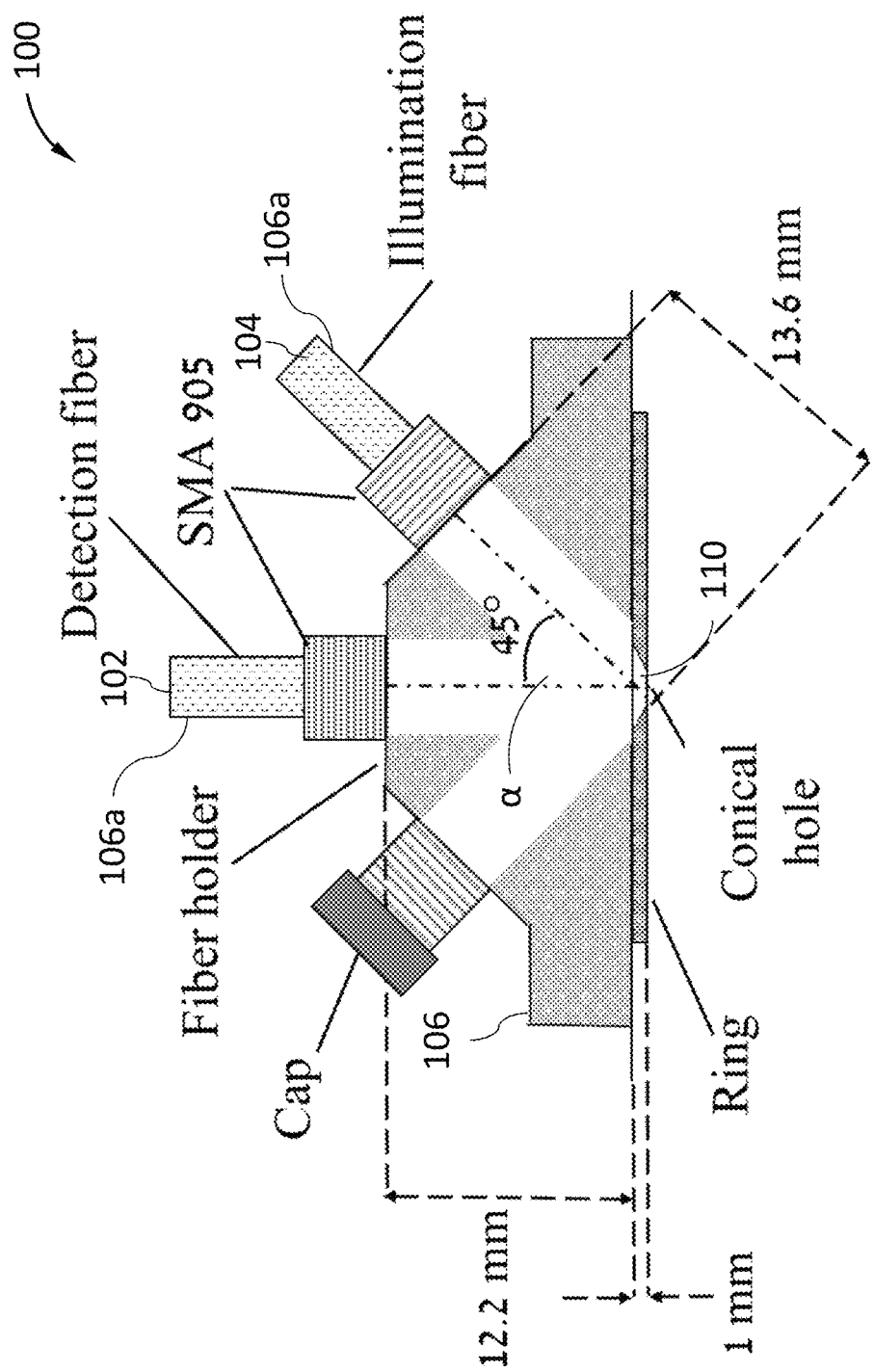
Figure 1C:
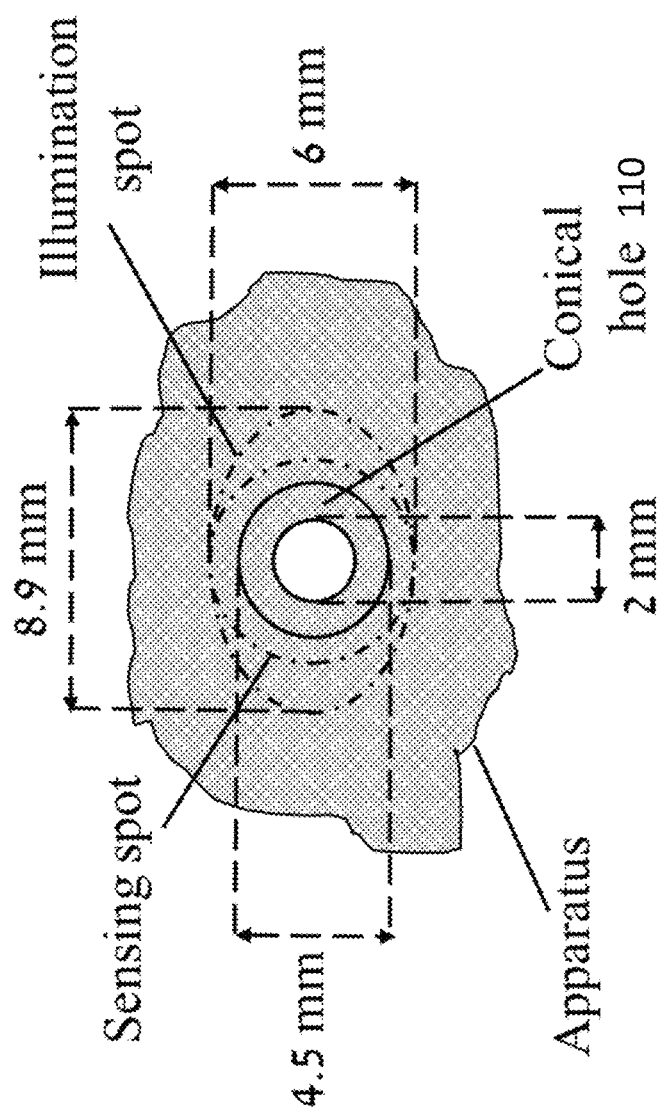

FIG. 1B-1C further illustrate exemplary embodiments of system 100. In some embodiments, system 100 may comprise a spectrometer 102 configured to measure the reflectance spectra of the fruitlets in situ. In some embodiments, the spectrometer has a spectral range of 400-1000 nm, a 1 nm spectral resolution, and a signal to noise ratio of 1000:1. In some embodiments, the spectrometer comprises a charge-coupled device (CCD) detector having an integrated thermoelectric cooling (TEC) that maintains the detector temperature at −15° C., to improve SNR.

In some embodiments, light source 104 may be a high-power tungsten halogen light source used for illumination of the sample fruitlet 108. In, light source 104 is configured to illuminate the sample fruitlet 108 surface at a 45° angle α to the normal, wherein the detection may be perfumed at 0° angle to the normal, using, e.g., fiber optic probes 106a with 25° angle field of view and a fiber holder 106. In some embodiments, during the measurement process, an underside of fiber holder 106 may be in contact with the sample fruitlet surface 108, wherein it is insured that fruitlet 108 maintains proper contact with the underside of holder 106.

FIG. 1C shows an underside of holder 106. In some embodiments, an underside of holder 106 may comprise aperture 110 comprising a conical shape with, e.g., a 120° degrees opening angle, to avoid obstruction of the illuminating light. In some embodiments, aperture 110 may have a diameter of, e.g., 2 mm and be, e.g., 1 mm thickness. In some embodiments, a light backscattering within system, 100 may be approx. %5 of the average light reflected by the sample fruitlet 108.

In some embodiments, sunlight contribution within system 100 may be calculated based on measuring reflectance with light source 104 alternatively open and blocked, to estimate sunlight contribution to the measurement.

In some embodiments, sunlight contribution and system backscatter contribution may be minimized by computing the fruitlet reflectance according to Equation 1:

$$R = 100 * c * ((F-A) - (S-D))/(W-A) \quad (1)$$

where c denotes calibration coefficients; F denotes a reflection signal of illuminated fruitlet; A denote system backscatter estimated with light trap; S denotes sunlight contribution; D denotes dark current measurement; and W denotes panel reflection signal.

Experimental Results

The present inventors performed a study on mature golden delicious apple trees, planted in 1997, and grafted on M9 rootstock. The trees were located at a commercial orchard and research station in the Upper Galilee area of Israel. The trees were 3.3 m high, and the planting density was 1,010 trees ha. The trees were irrigated and maintained according to general orchard practices. Measurements were conducted during two growing seasons—April 2017 and April 2018. Because the orchard is located in a semiarid region, the weather conditions during the growing period when the experiments were performed were in the range of 8-32° C. with 15-94% relative humidity (RH) in 2017, and 9-27° C. with 18-97% RH in 2018. Fruitlet monitoring was typically conducted from 12:00 till 17:00. Air temperature change during acquisitions did not exceed 3° C. on any specific day and ranged from 15° C. to 25° C. during the whole monitoring period.

Figure 2A:
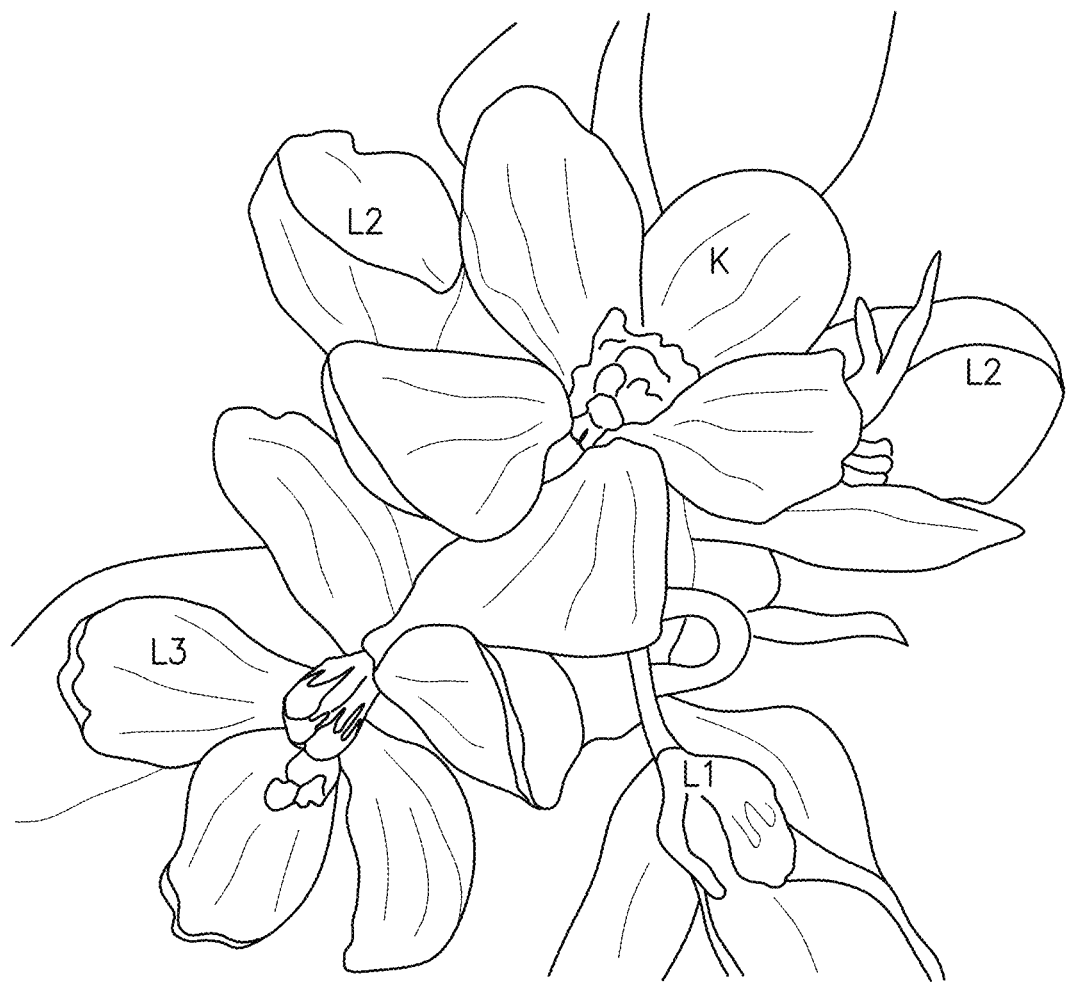
FIG. 2A-2B show apple fruitlet clusters.
Figure 2B:
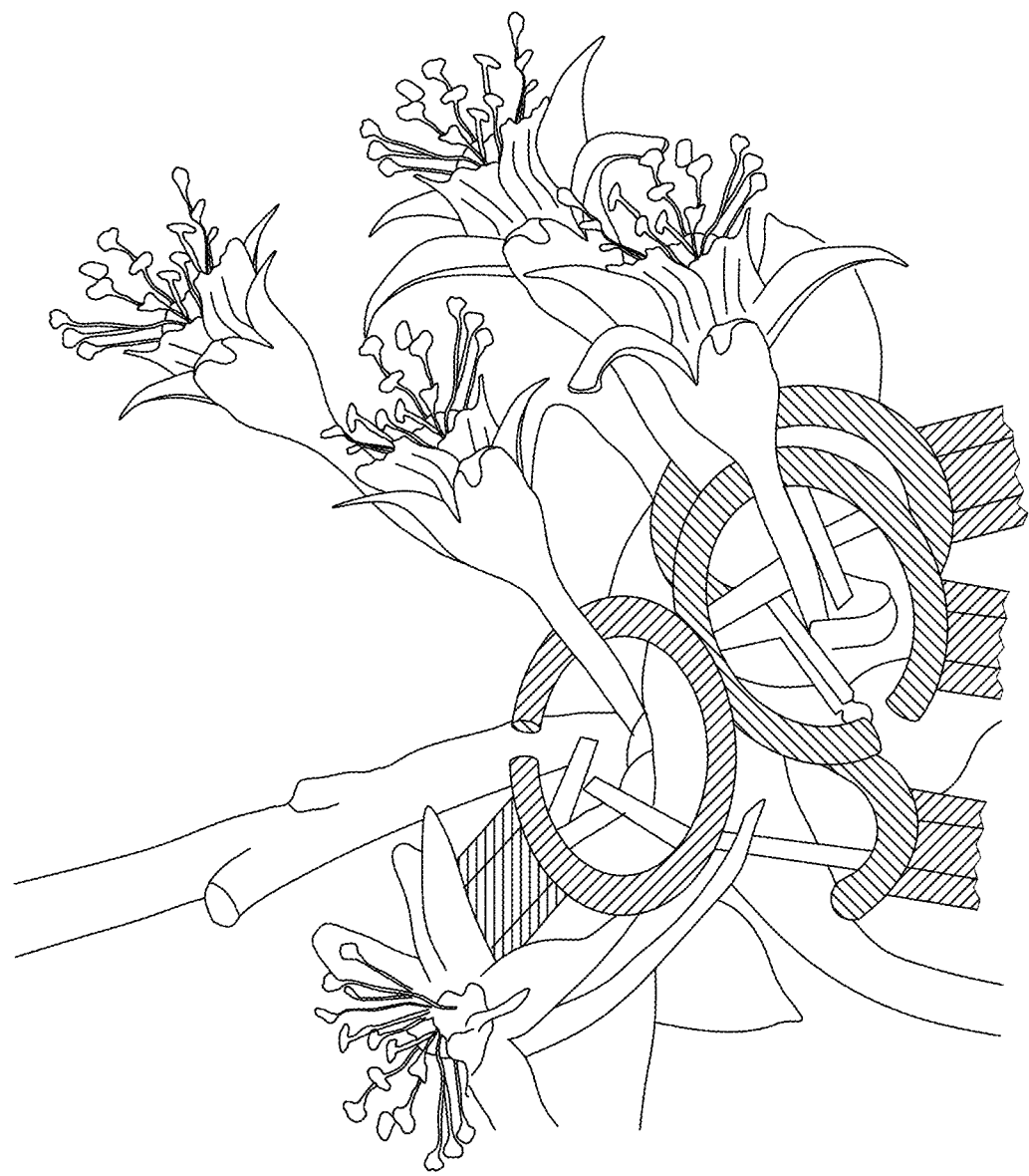

Apple fruitlets generally grow in a cluster of five fruits (FIGS. 2A-2B), and the fruitlet position within the cluster is known to influence its drop potential: central fruitlets (so-called king, K) and lateral fruitlets close to the central position (L3) have the highest probability to persist (FIG. 2A). On the other hand, under natural conditions, the dropping rate of laterals L1, located the farthest from the central fruitlet, is 80-100%. Accordingly, in the present work, K, L2 and L3 fruitlets were monitored, but L1 were not considered because commercial thinning management causes them to drop. FIG. 2B shows typical cluster image with rings tagging to distinguish between fruitlet types.

Fifty and seventy clusters were tagged on 10 and 9 trees in 2017 and 2018, respectively. Clusters from both inner and outer parts of the canopy were included. In 2017, monitoring of two of the clusters had to be stopped after their supporting branch broke. Tagging was done by placing the colored rings on the flower's pedicel one or two days before full bloom since it was the best time to distinguish between fruitlet types: king flower develops and reaches anthesis first, L3 flower is next, etc.

Fruitlet drop was amplified by the application of synthetic auxins 1-naphthaleneacetic acid (NAA) and its amide (NAD) at 3-4 days after full bloom (DAFB). This thinning is a common commercial treatment with 73 mg/L NAD+27 mg/L NAA (0.4% Agriton). The nonionic surfactant Triton X-100 was included in the formulation (0.025% v/v).

Vis-NIR measurements were conducted on the tagged fruitlets in situ every two to four days, starting from four days after the treatment (DAT). The fate of each labeled fruitlet was recorded during the measurements and for several weeks afterward, and a last visual observation was performed at the beginning of June after stabilization of the natural drop. The whole experiment timeline is summarized in Table 1.

TABLE 1

Experiment timeline in 2017 and 2018. DAT stands for days after treatment.

| Year | Full bloom | NAA + NAD treatment | Vis-NIR measurements dates (DAT) | Drop dynamics observation dates (DAT) |
|------|-----------|---------------------|----------------------------------|---------------------------------------|
| 2017 | April 10  | April 14            | 6, 10, 12                        | 14, 17, 20, 26, 51                    |
| 2018 | April 5   | April 8             | 4, 7, 9                          | 12, 16, 24, 50                        |

Generally, 400-600 measurements were performed on each measurement day, except on 6 DAT in which case only 165 measurements were performed due to technical issues. The measurement location was around the equator zone of each fruitlet. Measurements were performed on both sun-exposed and shaded regions of fruitlets to evaluate the effect of the measurement position on the observed reflectance. In 2017, four measurements were performed per fruitlet, two on the sun-exposed region and two on the shaded region. The king and the two laterals L2 fruitlets were monitored in each cluster. In 2018, the number of measurements per fruitlet was restricted to two, which made it possible to monitor a higher number of fruitlets. Both measurements were performed either on the sun-exposed or shaded side of half of the fruitlets. The king and the laterals L3 and L2 were monitored in each cluster that year. Details about the measurements are provided in Table 2.

TABLE 2

Experiment details in 2017 and 2018. DAT stands for days after treatment.

| Year | Daily measurements | Number of measurements per fruitlet | Fruitlet region measured |
|---|---|---|---|
| 2017 | 550-559 (165 only in 6 DAT) | 4 | Sun-exposed and shaded for each fruitlet |
| 2018 | 400-623 | 2 | Sun-exposed for half of the fruitlets, and shaded for the second half |

Fruitlet Drop Dynamics

Figure 3B:
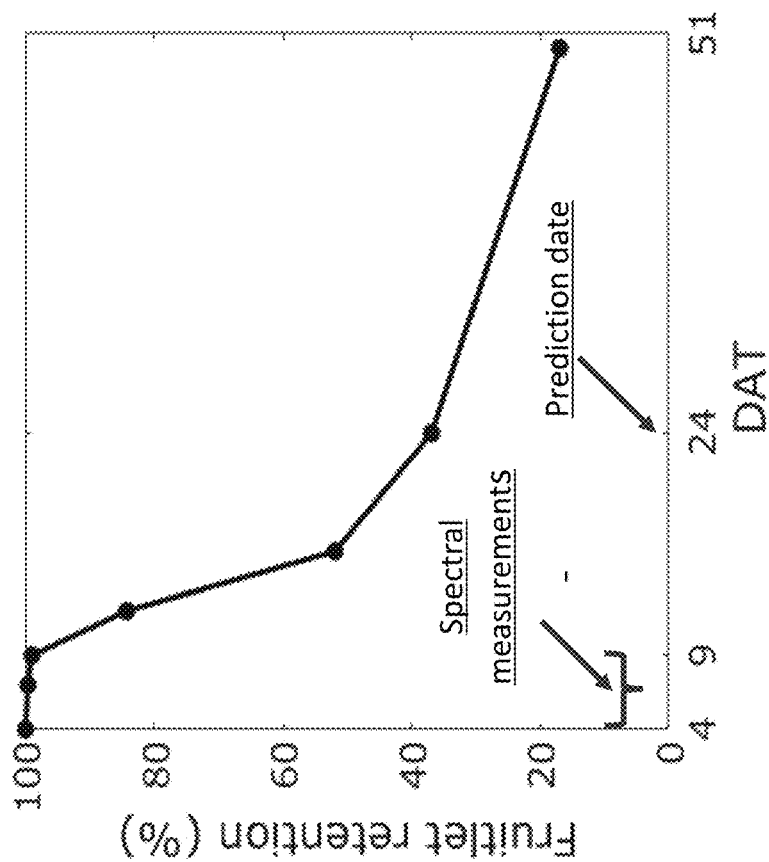
FIG. 3A-3B show fruitlet retention rates in apples.
Figure 3A:
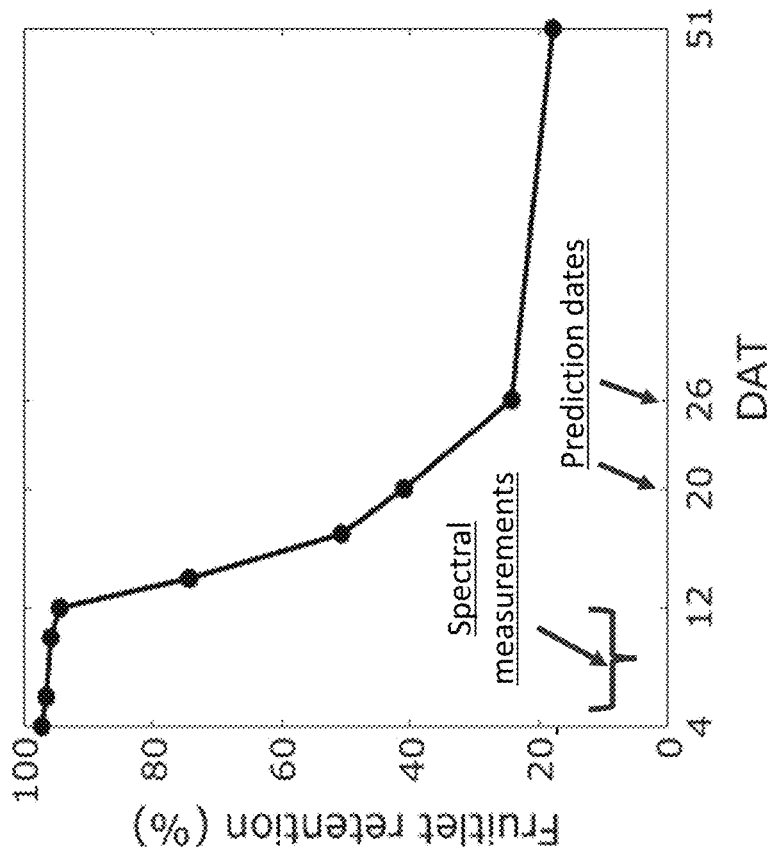

FIG. 3A shows fruitlet retention rate for all fruitlets (King and both laterals L2) monitored in 2017. FIG. 3B shows fruitlet retention rate for all fruitlets (King, both laterals L2, and lateral L3) monitored in 2018. The fruitlet retention rate for both years, as determined by visual observations and manual counts, is shown in FIGS. 3A-3B. These observations agree with previous reports and additional observations conducted by the present inventors in 2015 and 2016, which all showed that fruitlet drop after 22-24 DAT usually equals 10-15%. In 2018 it was atypically higher due to insufficient accumulation of chilling hours and strong day-to-day changes in meteorological conditions. In 2017, the measurements at 6-12 DAT, before any significant fruitlet drop occurred, were used to predict fruitlet drop by 20 and 26 DAT. In 2018, the measurements at 4-9 DAT were used to predict fruitlet drop by 24 DAT. In each case measurements from only one specific date were used to forecast fruitlet status at the prediction date.

Data Analysis

Figure 4:
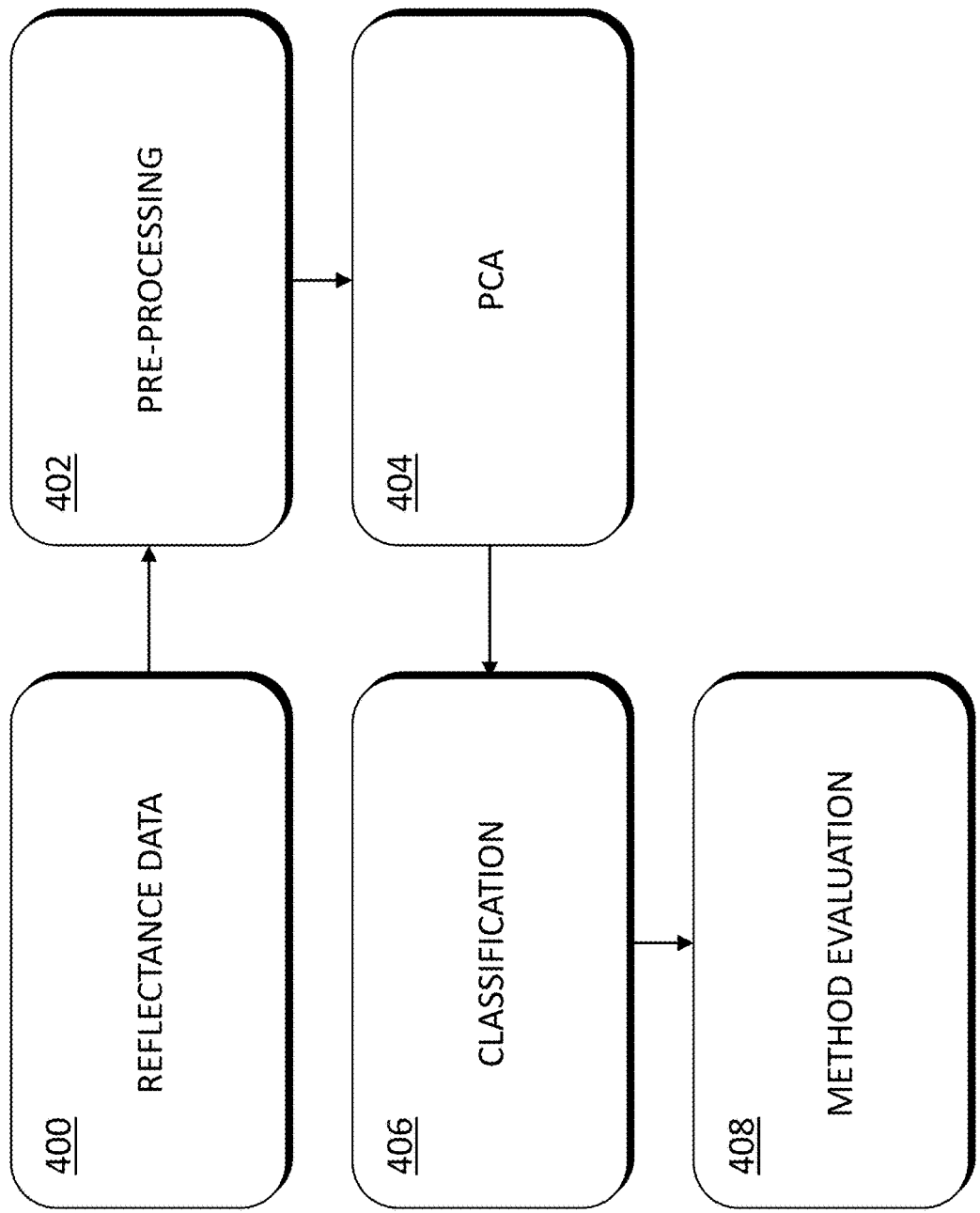
FIG. 4 is a flowchart of the data processing, in accordance with some embodiments of the present disclosure.

FIG. 4 is a flowchart of the data processing according to the present disclosure, which was performed in Matlab 2017b (Math-Works, Inc., USA).

In some embodiments, at step 400, reflectance data may be acquired from a plurality of fruitlet samples, and fruitlet reflectance is calculated according to Eq. (1) above.

In some embodiments, at step 402, a preprocessing step may be performed with respect to the acquired data, which may comprise, e.g., a filtering operation, e.g., a Savitsky-Golay filtering (order 2, window size 21). Optionally, preprocessing ma comprise logarithmic (log(1/R)) or reciprocal (1/R) transformation.

In some embodiments, at step 404, a dimensionality reduction step may be performed to, e.g., extract principal components that best describe the data while reducing data dimensionality. In some embodiments, this step may be performed using, e.g. principal component analysis (PCA).

In some embodiments, at step 406, the extracted PCA scores may be used as a training set to train a machine learning model, e.g., a classifier. In some embodiments, the machine learning model may use any suitable algorithm e.g., linear discriminant analysis (LDA), quadratic discriminant analysis (QDA), or QDA without taking into account class prior probabilities (MQDA). In some embodiments, the training dataset was annotated with labels indicating with respect to each the likelihood of remaining on the tree or dropping.

In some embodiments, the LDA and QDA classification scores ($L_{ik}$ and $Q_{ik}$) for a sample i and a class k, are computed based on the prior probability of the class and the Mahalanobis distance to the class:

$$L_{ik} = (x_i - \bar{x}_k)^T \Sigma_p^{-1} (x_i - \bar{x}_k) - 2 \ln \pi_k \quad (2)$$

$$Q_{ik} = (x_i - \bar{x}_k)^T \Sigma_k^{-1} (x_i - \bar{x}_k) + \ln |E_k| - 2 \ln \pi_k \quad (3)$$

where $x_i$ is the vector of features for sample i, $\bar{x}_k$ is the mean vector of class k, $\pi_k$ is the prior probability of class k, $\Sigma_p$ is the pooled covariance matrix and $\Sigma_k$ is the variance-covariance matrix of class k.

In some embodiments, LDA and QDA are supervised classification methods based on finding linear combinations of the independent variables that maximize the between-group variance relative to the within-group variance. The difference between LDA and QDA methods is in assuming equal variance-covariance matrices among input variables of the classes for LDA, while QDA computes the variance structures for each class separately. Ignoring prior probabilities in Eq. (3) yields a classifier labeled in this work as MQDA.

Because the outcome for a fruitlet is to remain on a tree or to drop, a binary vector may be assigned to each measurement. The number of principal components (PCs) was restricted to 6-7 at the most to avoid including noise in the model. The model performance was evaluated on the validation dataset (40% of the data) using accuracy, sensitivity and specificity indices:

$$\text{Accuracy} = \frac{TP + TN}{TP + TN + FP + FN} * 100\% \quad (4)$$

$$\text{Sensitivity} = \frac{TP}{TP + FN} * 100\% \quad (5)$$

$$\text{Specificity} = \frac{TN}{TN + TP} * 100\% \quad (6)$$

where TP—true positive, TN—true negative, FP—false positive, FN—false negative.

PCA and classification were tested for several spectral ranges: 400-1000 nm, 450-800 nm, 600-950 nm, and 600-800 nm. These ranges were selected to eliminate regions with high noise (low detector response) and exclude the 500-600 nm region in which large variability was observed due to anthocyanin accumulation in the sun-exposed fruitlet region (more detailed information is given in the "results and discussion" section).

Results and Discussion

Figure 5A:
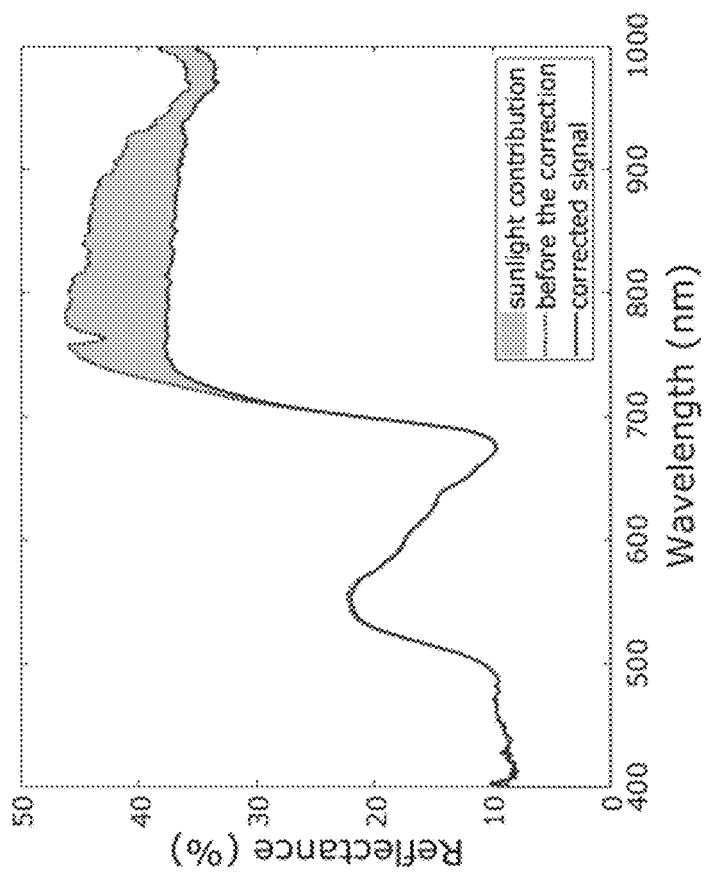
Figure 5B:
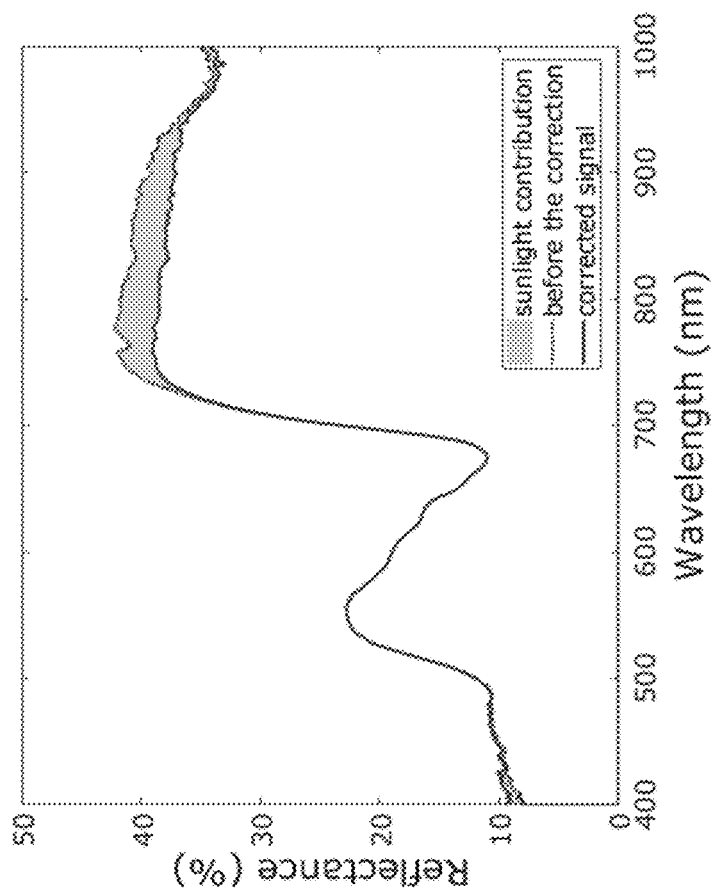
Figures 6A, 6B:
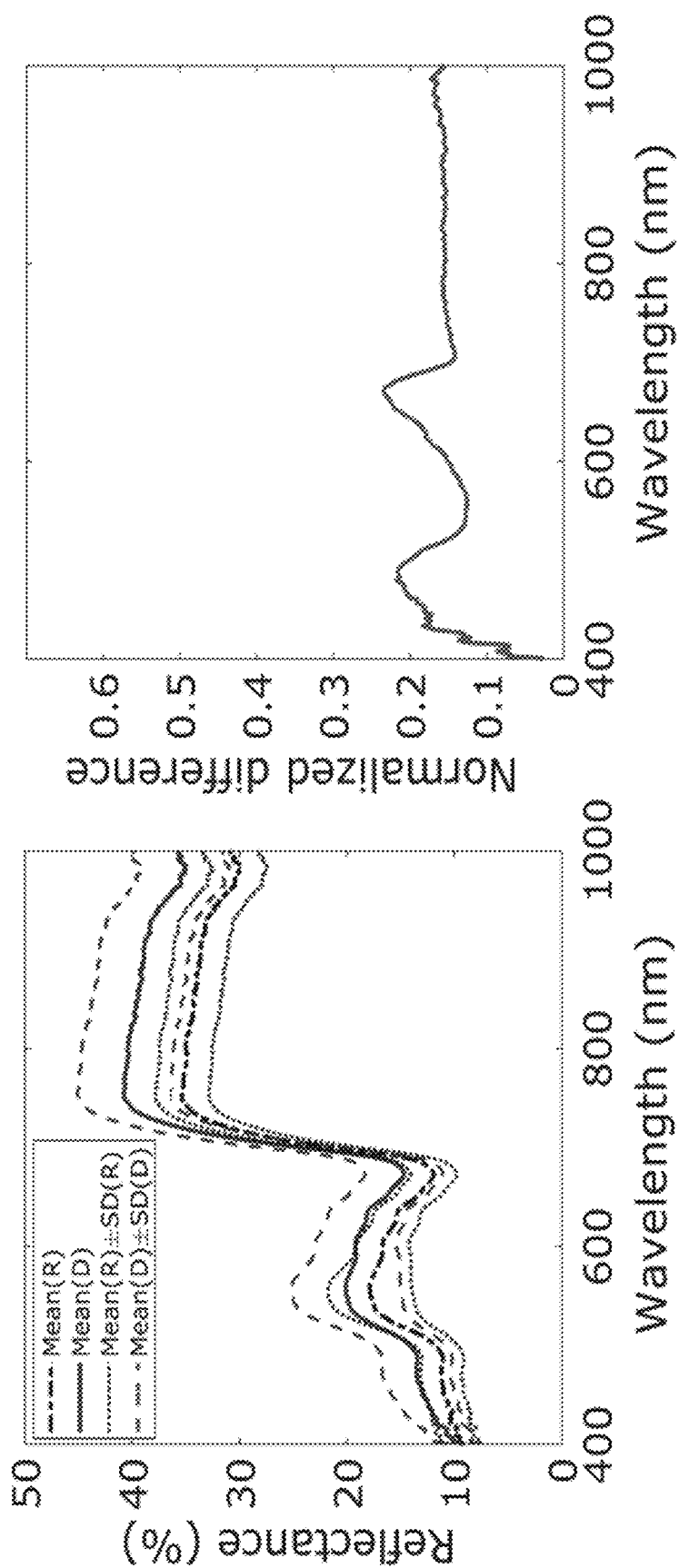
Figure 6C:
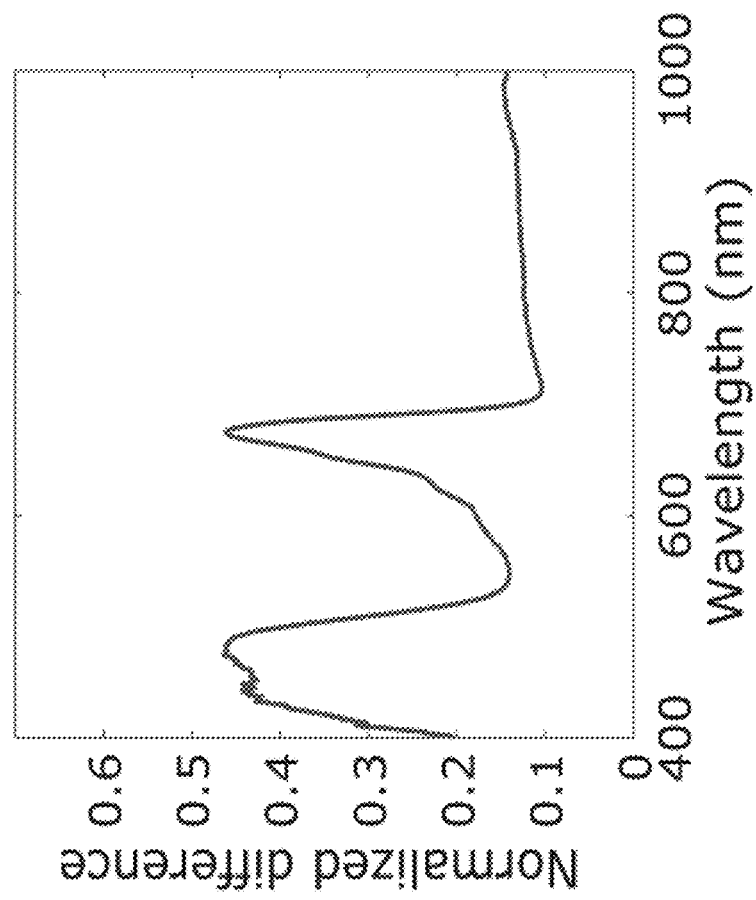
Figure 6D:
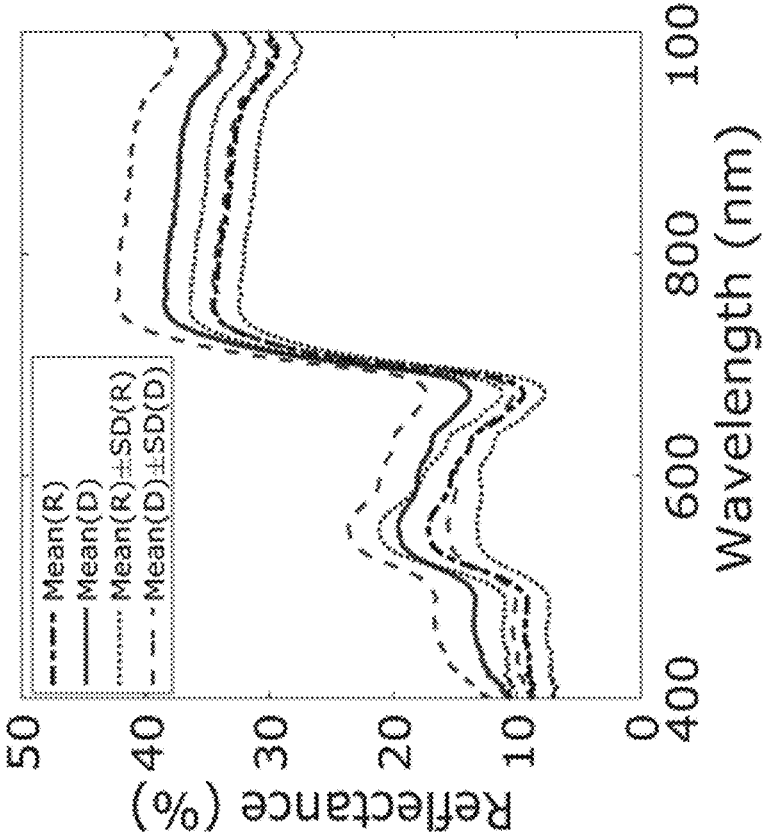
Figures 6E, 6F:
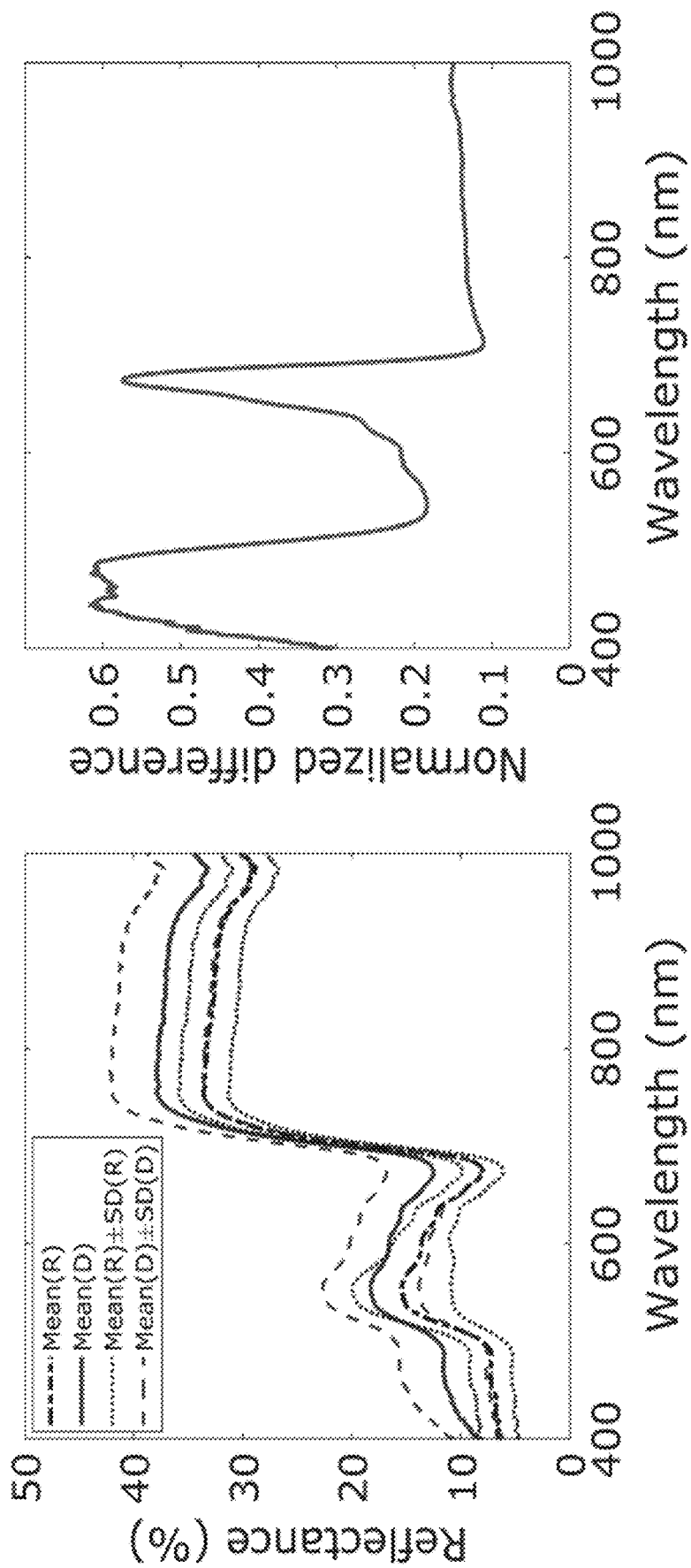

FIGS. 5A-5B show typical examples of 'raw' fruitlet reflectance affected by sunlight contribution and after applying the procedure developed for reducing this effect (Eq. (1)). The difference between the two curves, highlighted by the gray area, shows that various measurements were affected by sunlight contribution to a different extent (FIG. 5A vs. FIG. 5A).

As can be seen from FIGS. 5A-5B, sunlight added a substantial and variable contribution to the reflectance in the NIR range, while the visible range remained unaffected. When sunlight contribution is significant, a characteristic dip in the spectra appeared at 763-764 nm, caused by the absorption of molecular oxygen in the atmosphere. The corresponding feature was used to evaluate the performance of the procedure. Typically, sunlight contribution was successfully reduced in >99% of the measurements, while the remaining <1% of the measurements were discarded due to the change in fiber holder position during the acquisitions. Sunlight also warms the fruitlets, which influences the measurements in the NIR range. This effect should be thoroughly investigated in future studies.

FIGS. 6A-6F show mean reflectance curves (after applying sunlight correction) of the dropping and retaining fruitlets at 6, 10 and 12 DAT in 2017. These curves used fruitlet status at 26 DAT as reference. Normalized difference (ND) curves, estimated by the Eq. 7 are shown as well:

$$ND=(\overline{R}_d-\overline{R}_r)/\overline{R}_r \tag{7}$$

where $\overline{R}_d$, $\overline{R}_r$—average reflectance curves of dropped and retained fruitlets.

Mean reflectance curves at 4, 7 and 9 DAT (2018) are shown in FIG. 7. The reference date was 24 DAT.

Figures 7A, 7B:
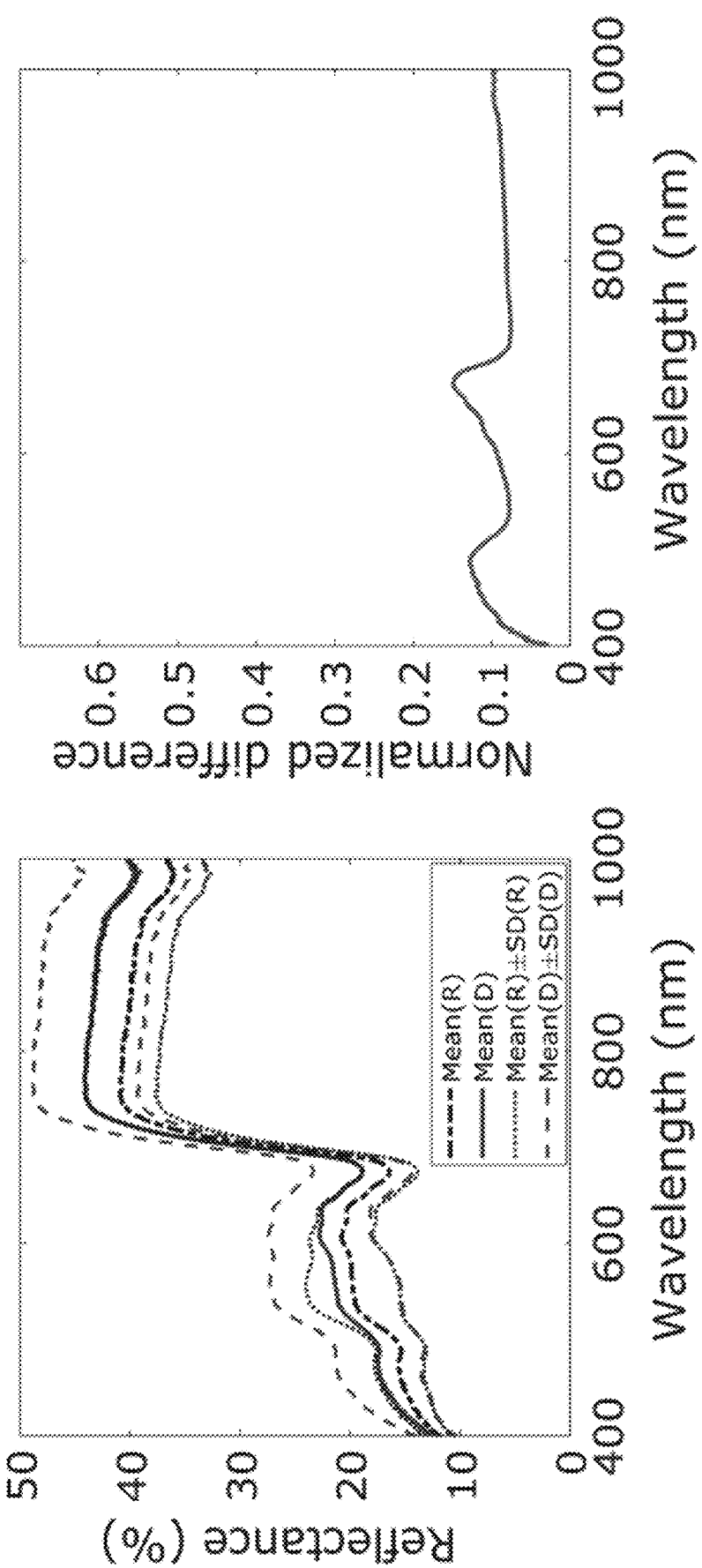
Figure 7D:
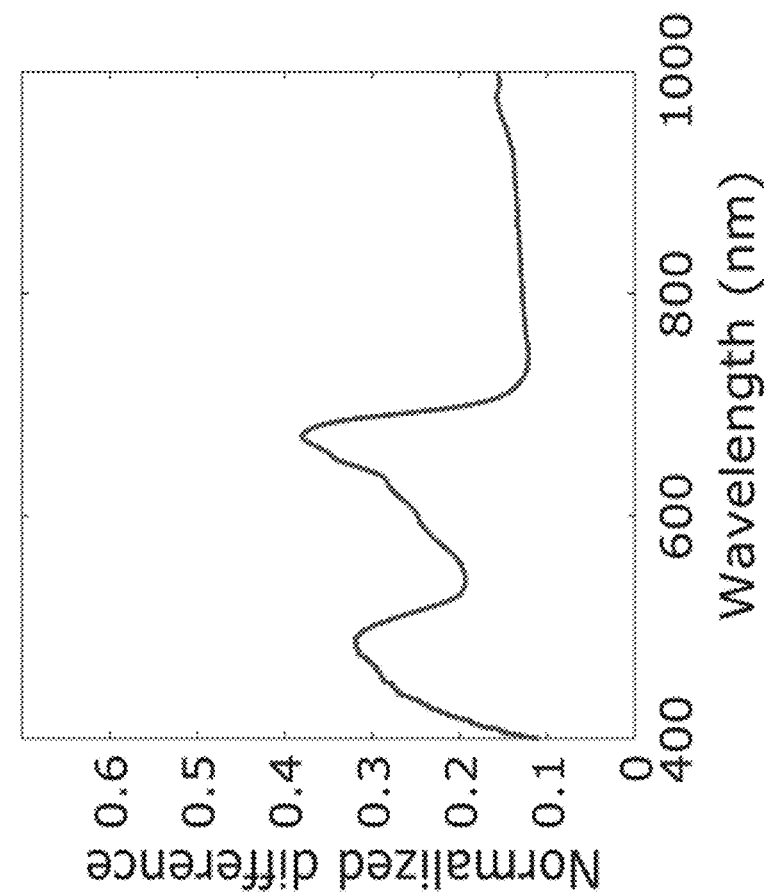
Figure 7C:
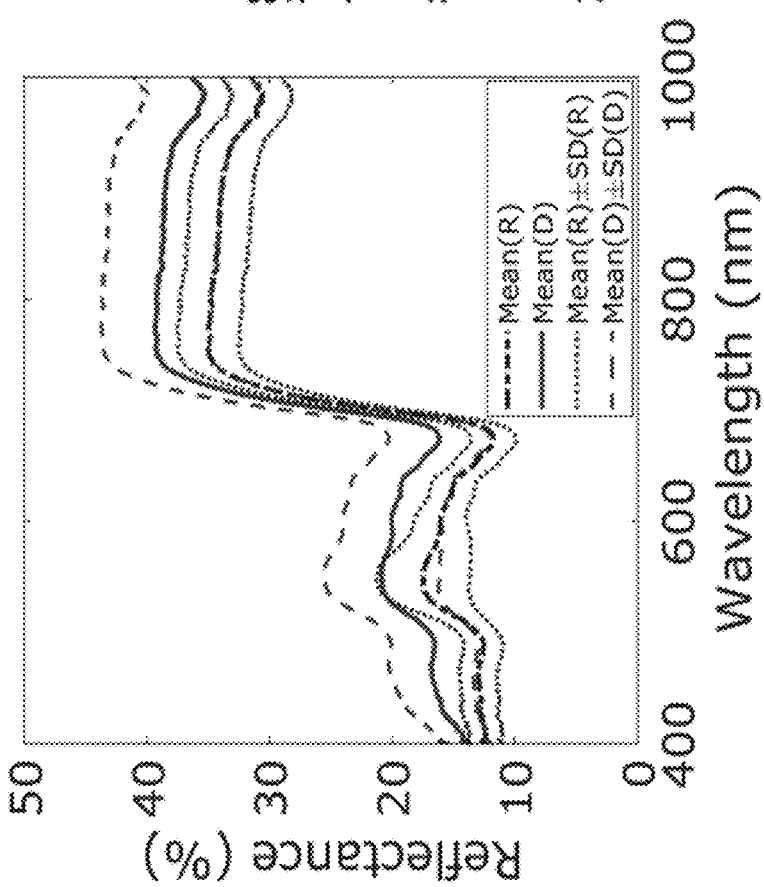
Figures 7E, 7F:
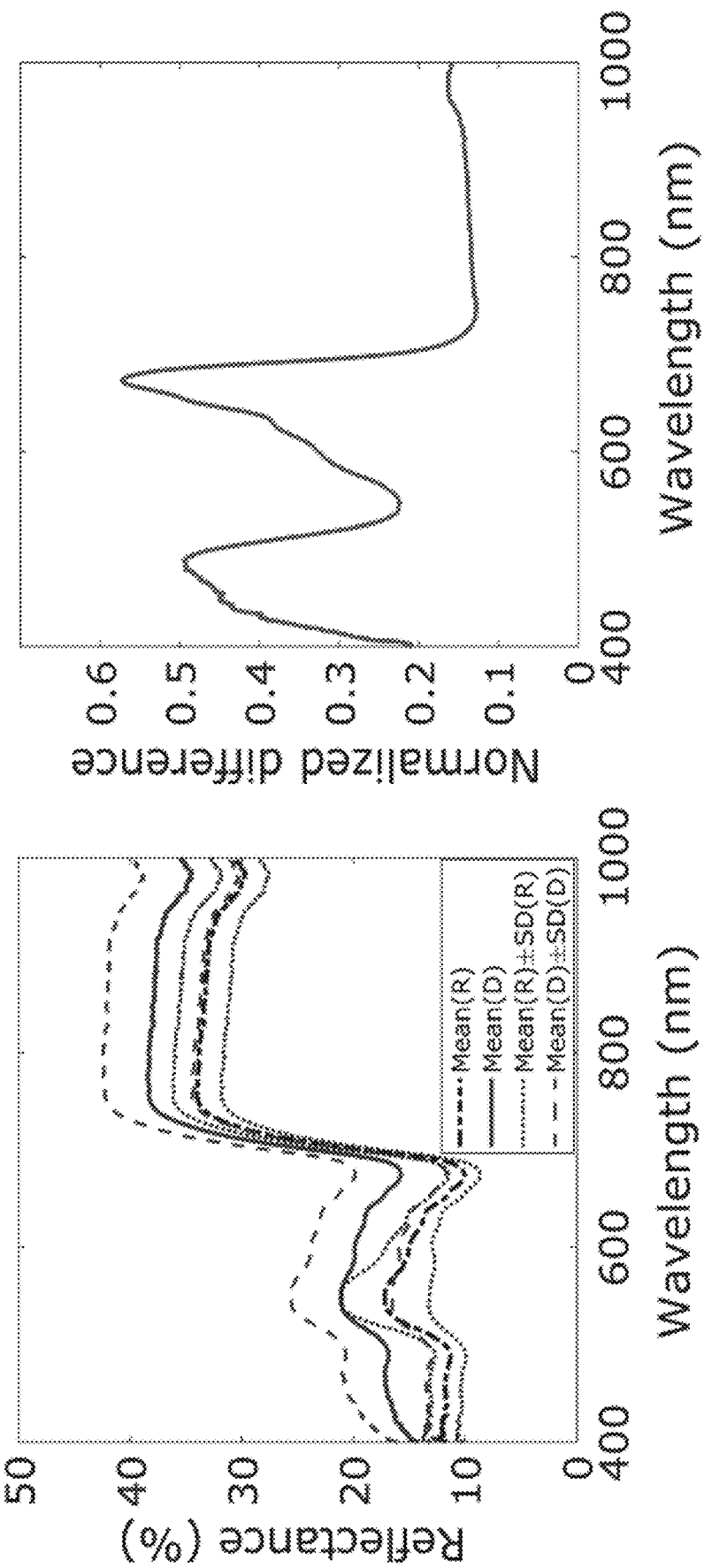

FIGS. 7A, 7C, and 7E show Mean and mean±standard deviation (SD) reflectance curves for dropping (D) and retaining (R) fruitlets at 4 (7A), 7 (7C) and 9 DAT (7E) (2018). FIGS. 7B, 7D, and 7F show corresponding normalized mean reflectance difference (Eq. 7). The reference date is 24 DAT.

The average reflectance curves and normalized differences pointed out to significant changes in fruitlet reflectance between measurement dates due to the fruitlet development. Overall, dropping fruitlets had higher reflectance in the whole Vis-NIR range (FIG. 6 and FIG. 7), and this difference became more pronounced at 7-12 DAT, compared to 4-6 DAT, especially in the visible range. In both years, two major differences in the red and blue spectral ranges, with maxima at 675 and 480 nm, stood out according to the normalized difference curves. Normalized differences in the blue and red spectral ranges had similar values in 2017, but a slightly lower value was observed for the blue range in 2018. It can be explained by seasonal variability.

Differences in the green and NIR spectral ranges were less pronounced, including reflectance decline near 970 nm due to water absorption. Therefore, the red and/or blue spectral range intuitively seem to be optimal ranges for spectral separation. The blue range of the spectrum is known to be affected by chlorophyll and carotenoids absorption, while the red spectral range is affected by chlorophyll pigment solely.

Looking at the curves standard deviation, higher standard deviations were obtained for fruitlets destined to drop. Since drop takes time (FIG. 3), the larger standard deviations probably reflect differences in the development of the dropping fruitlets, including differences among fruitlets within the cluster and among clusters.

Figure 8:
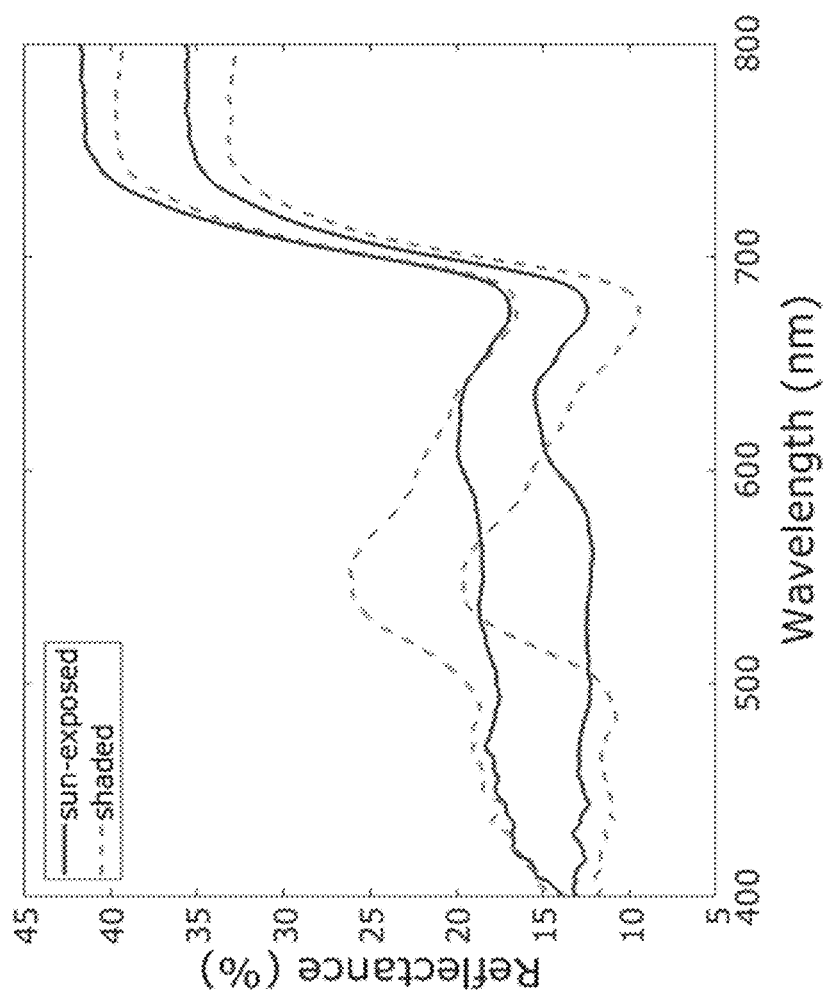

FIG. 8 displays typical curves of the sun-exposed (receiving direct sunlight) and shaded (receiving diffusive sunlight) fruitlet regions at 9 DAT (2018). For shaded regions, maximum reflectance is obtained in the green region around 550 nm. At higher wavelengths reflectance decreases up to a minimum at 675 nm, caused by a strong chlorophyll absorption. On the other hand, anthocyanin build-up in the sun-exposed regions causes a reflectance decrease in the 500-600 nm region. Anthocyanin accumulation is a photoprotection mechanism and a preliminary analysis showed no relation between anthocyanin accumulation and fruitlet drop (details not shown).

Classification Results

PCA was performed for four different spectral ranges: 400-1000 nm, 600-950 nm, 450-800 nm, and 600-800 nm to determine whether higher noise at the ends of the spectrum and anthocyanin accumulation on the sun-exposed side affected the results. Table 3 shows how spectral range selection affected the accuracy (Eq. 4) of the classification in validation datasets (40% of the data, averaged for 100 runs) in both years. Sensitivity and specificity (Eqs. 5-6) had a similar trend. Log(1/R) transformation was applied to the spectra since this transformation resulted in slight accuracy improvement (details not shown). Based on preliminary analysis, LDA classification method was selected and the number of PCA factors was set to 6 (except when using 6 DAT (which included fewer measurements, see Table 2) for which 3 PCA factors were found to be optimal).

It can be seen from Table 3 that the effect of the spectral range on the accuracy results was small, meaning that PCA and classification models were unaffected by the higher spectral noise occurring at the ends of the spectral range and anthocyanin accumulation.

TABLE 3

Effect of different spectral ranges on classification accuracy (CA) for validation datasets of 2017 and 2018.

| | Year | | | | | | | |
|---|---|---|---|---|---|---|---|---|
| | 2017 | | | | | | 2018 | |
| | Prediction date (DAT) | | | | | | | |
| | 20 | | | 26 | | | 24 | |
| | Measurement date (DAT) | | | | | | | |
| Spectral range (nm) | 6 | 10 | 12 | 6 | 10 | 12 | 7 | 9 |
| | CA (%) | | | | | | | |
| 400-1000 | 87 | 98 | 96 | 81 | 82 | 81 | 79 | 86 |
| 600-950 | 88 | 97 | 97 | 81 | 83 | 80 | 79 | 89 |
| 450-800 | 84 | 98 | 97 | 80 | 82 | 80 | 80 | 89 |
| 600-800 | 86 | 97 | 97 | 82 | 83 | 80 | 80 | 91 |

DAT stands for days after treatment.

Figure 9B:
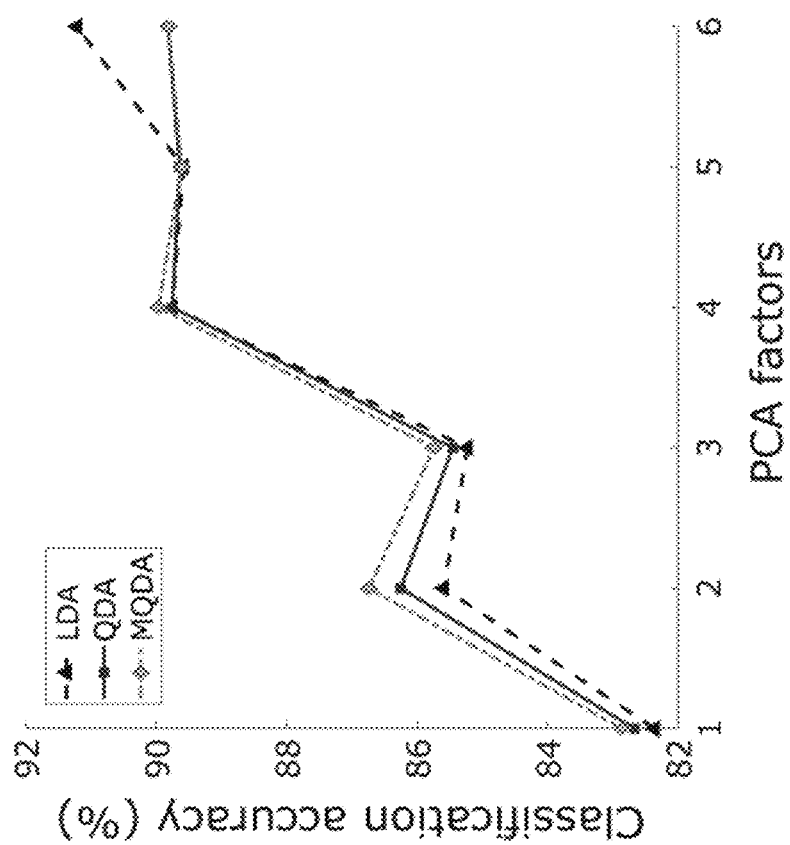
Figure 9A:
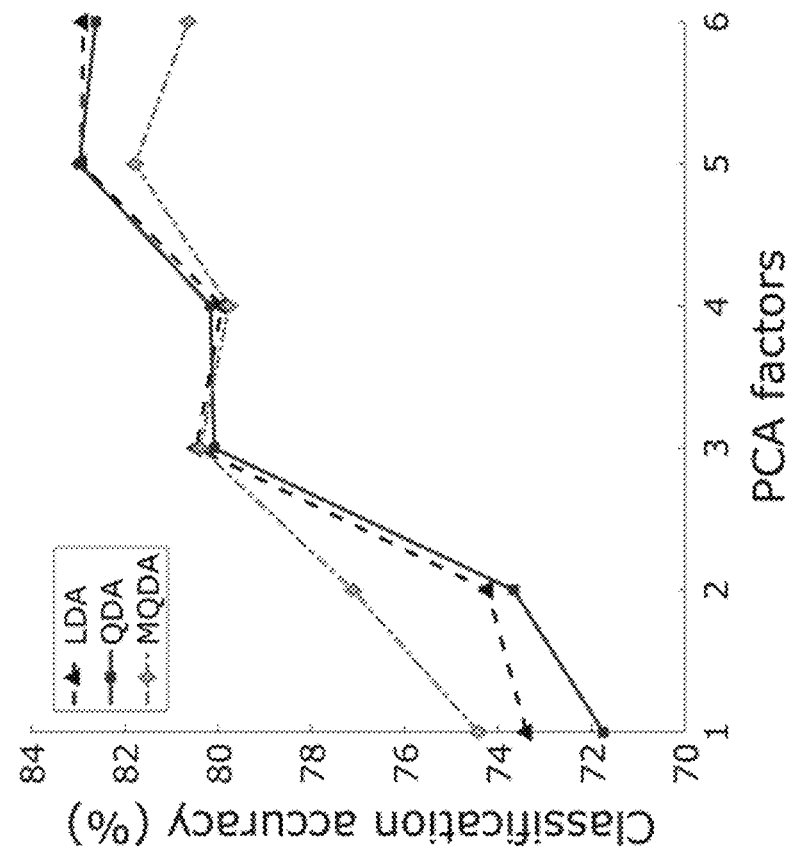

Examples of classification accuracy in the validation datasets vs. number of PCA factors and different classification methods are displayed in FIGS. 9A-9B. FIG. 9A shows the accuracy of the prediction of fruitlet status at 26 DAT (2017) based on the measurements performed on 10 DAT (2017), using the 600-800 nm spectral range and applying log(1/R) transformation. FIG. 9B shows the accuracy of the prediction of fruitlet status at 24 DAT (2018) based on the measurements performed on 9 DAT with the same range and transformation applied.

It can be seen from FIGS. 9A-9B that the validation accuracy improved with increasing the number of PCA factors, and five-six PCA factors were optimal. Regarding the classification methods, the difference between different methods was small and changed with the number of PCA factors. It was decided to select the LDA classification method and 6 PCA factors to be used in further data analysis.

Figures 10A, 10B:
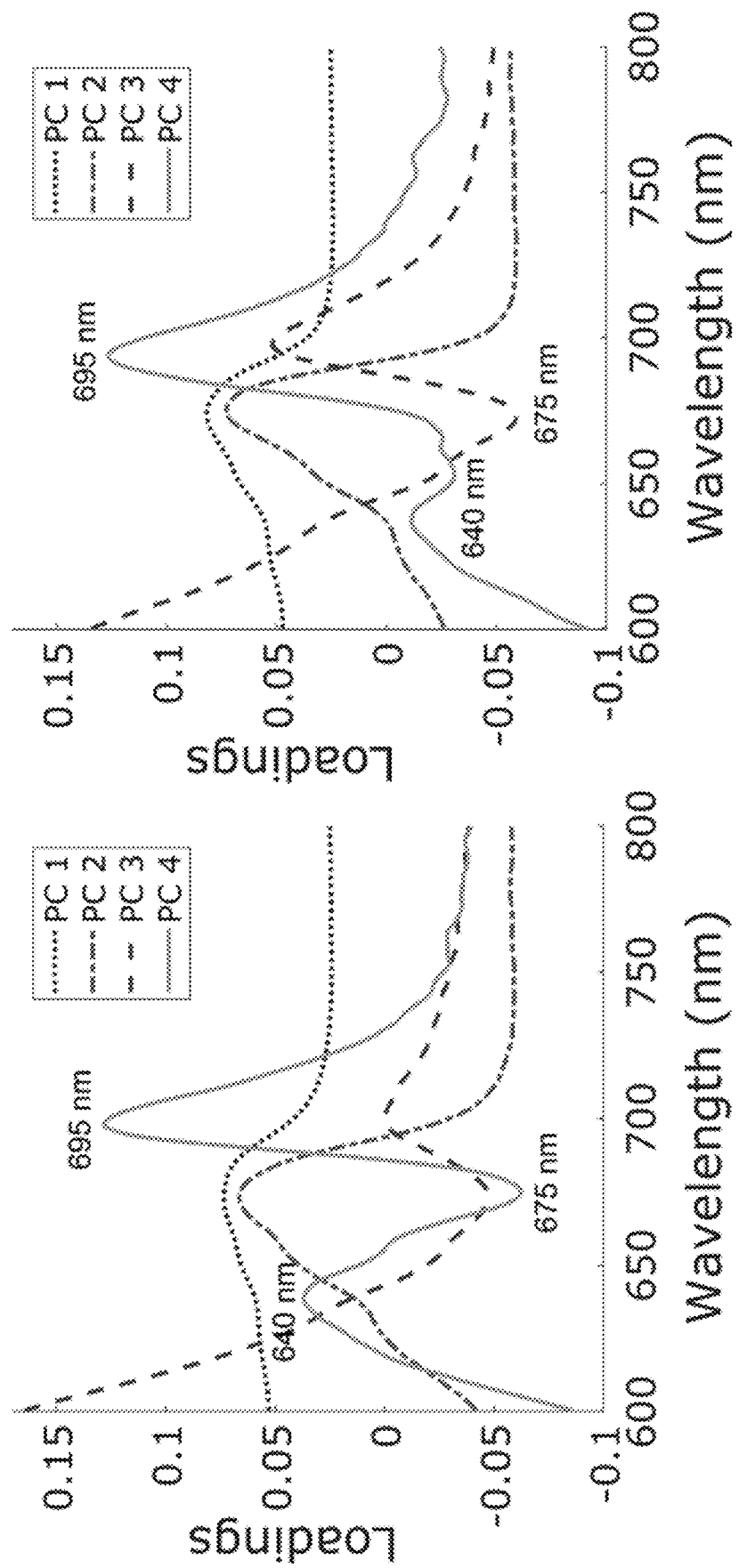

Examples of the first four PCA loadings obtained from the measurements of 10 DAT (2017) and 9 DAT (2018) are shown in FIGS. 10A-10B. The first principal component (PC) probably reflected the average spectrum behavior with a small peak at 675 nm in both years. PCA loadings 2-4 also have similar patterns in both years with peaks and valleys at the red (640 nm and 675 nm) and red-edge (695 nm) spectral regions, and the addition of these features enhanced the results of the classification. Wavebands at 675 nm and ~700 nm are known to be connected to the absorption of chlorophyll pigment.

Table 4 summarizes model performance on the validation datasets using measurements at 6-12 DAT in 2017, and 4-9 DAT in 2018. The performances of the models were evaluated using accuracy, sensitivity and specificity (Eqs. 4-6), averaged for 100 runs. The differences between results obtained with different pretreatments, spectral ranges (Table 3) and classification methods (FIG. 9 as an example) were small, therefore only the results obtained using a single transformation pretreatment (log(1/R)), spectral range (600-800 nm) and classification method (LDA) are presented here for all the dates.

TABLE 4

Classification models performance (CA—classification accuracy, Sens—sensitivity, Spec—specificity) for validation datasets of 2017 and 2018. DAT stands for days after treatment.

| Measurement date (DAT) | Prediction date (DAT) | Prediction interval (days) | CA (%) | Sens (%) | Spec (%) |
| --- | --- | --- | --- | --- | --- |
| 6 (2017) | 20 | 14 | 86 | 80 | 91 |
| 6 (2017) | 26 | 20 | 82 | 65 | 93 |
| 10 (2017) | 20 | 10 | 97 | 98 | 96 |
| 10 (2017) | 26 | 16 | 83 | 61 | 96 |
| 12 (2017) | 20 | 8 | 97 | 96 | 97 |
| 12 (2017) | 26 | 14 | 80 | 56 | 96 |
| 4 (2018) | 24 | 20 | 65 | 47 | 79 |
| 7 (2018) | 24 | 17 | 80 | 69 | 88 |
| 9 (2018) | 24 | 15 | 91 | 85 | 95 |

In 2017, when taking fruitlet status on 20 DAT as a reference, the average accuracy in fruitlet drop prediction was 86-97%, depending on the date of the measurement. The accuracy was higher when the measurement was closest to the forecast date. This is not surprising since physiological differences in fruitlet development become more pronounced with time. When using fruitlet status at 26 DAT as reference (2017), the average accuracy was 80-83%. In that case, the forecast was performed with 14-20 days lead-time, compared to 8-14 days in the previous case. Although the accuracy of the prediction is lower for 26 DAT, it is still satisfactory. In 2018, the accuracy was 80-90% for 17-15 day lead-time and dropped to 65% for 20 day lead-time when using the measurements performed at 4 DAT. This indicates that measurements at 4 DAT are too early to differentiate between persisting and dropping fruitlets with good accuracy, and/or 20-day lead-time is too long. Further investigation should be conducted in this respect. Regarding the sensitivity and specificity values, specificity was always close to 80% and above, which is considered "good" (Luo et al., 2012). However, sensitivity for lead-times of 14-20 days often dropped below 80%. This can be partially explained by the fact that the number of remaining fruitlets is proportionally lower, leading to weaker statistics.

Accordingly, in-situ Vis-NIR spectral measurements obtained using a specified set-up were used to forecast apple fruitlet drop following application of a thinning bio-regulator. The authors recommended to shade the fruits artificially to minimize sunlight effect, while we suggested here a different approach based on performing an additional measurement without artificial illumination and applying a post-processing correction procedure. Reflectance spectra covering several spectral ranges were subjected to PCA, followed by supervised classification using LDA, QDA or MQDA. The effect of spectrum pretreatment, spectral range, and classification method was found to be small.

Using measurements performed at 6-12 DAT led to prediction accuracy ranging from 80% (20 days lead-time) to 97% (8 days lead-time). The corresponding time window would be suitable for decisions regarding the additional thinner application. It should be noted that the classification models were based on in-situ measurements acquired while monitoring small-size objects. Moreover, the models were based on measurements performed on both sun-exposed and shaded regions of fruitlets located within the canopy and on its edge. These factors highlight the robustness of the proposed technique for future applications.

To conclude, this study demonstrated the feasibility of using in-situ Vis-NIR measurements for predicting fruitlet drop rate. The technique is fast and non-destructive and despite the uncontrolled working environment and small size of the fruitlets, very high accuracy was achieved. Future work shall be devoted to identifying the most informative wavelengths as a first step toward the development of a small, portable, measuring device suitable for practical applications.

Further Experimental Results

The present inventors have conducted a further study to identify the most informative wavebands in the Vis-NIR spectrum and to establish their potential for fruitlet destiny prediction. Different approaches exist for wavebands selection in classification problems, including correlation analysis, PCA, interval partial least square discriminant analysis (iPLS-DA), stepwise variable selection algorithm and receiver operating characteristic (ROC) curve.

In addition, a complementary investigation of the impact of fruitlet trichomes density on the observed spectra was conducted to gain insight into the causes of the observed differences and support the selection of the optimal wavebands.

The same spectral measurements were used as in the study detailed above. The spectral range was 400-1000 nm sampled with 1 nm spectral resolution. The set-up had 45°/0° to normal illumination/detection configuration using fiber optics and custom holder. The measurement was performed in contact with the fruitlet surface. Inconsistent sunlight contribution to the measured intensity was assessed by performing an additional measurement after blocking the light source with a shutter, and this contribution was eliminated during spectra post-processing as detailed in.

Four measurements per fruitlet were performed in 2017, while two measurements per fruitlet were performed in 2018. Measurements were performed on both sun-exposed and shaded fruitlet regions. The number of daily measurements was generally 400-600 measurements (except 6 days after treatment where only 165 measurements were performed due to technical issues). Apple fruitlets grow in clusters of five, and the fruitlet position in the cluster affects its drop rate. The central fruitlet (commonly labeled King) and the lateral close to the central position (labeled L3) have the highest probability to retain, compared to other fruitlets in the cluster (two laterals labeled L2 and lateral L1). The smallest lateral (L1) drops very often and therefore was not included in the present study. Measurements were conducted on King and laterals L2 in 2017 and King and laterals L2 and L3 in 2018.

Experiment Timeline

Commonly-used commercial thinning with synthetic auxins 1-naphthaleneacetic acid (NAA, 27 mg/L) and its amide (NAD, 73 mg/L) was performed at 3-4 days after full bloom (DAFB). It must be noted that preliminary work showed that thinner application does not change the trend of the fruitlet drop, but only amplifies it. Fruitlets development was monitored every 2-4 days during approximately three weeks starting at 4 DAT and a final fruitlet count was performed at the end of June drop. FIG. 1 shows the fruitlet counts throughout the course of both experiments. Two reference dates, 20 and 26 DAT were selected as reference dates for 2017 and the measurements at 6, 10 and 12 DAT were used to forecast the drop by these dates (FIG. 1a). In 2018, 24 DAT was selected as the reference date for 2018, and the measurements at 4, 7 and 9 DAT were used to forecast the drop by this date (FIG. 1b). The selection of these reference dates was based on the drop dynamics that can be observed in FIGS. 11A-11B, which show that under non-extreme weather conditions the drop rate is very low starting 23-24 days after treatment. Note that the unusual weather in 2018 resulted in unusually high late drop. However, such a situation is highly exceptional and from a decision-making point of view, the massive chemically-amplified drop that takes place around 10-24 DAT is of major interest while the late drop can be roughly estimated from historical records.

Figures 11A, 11B:
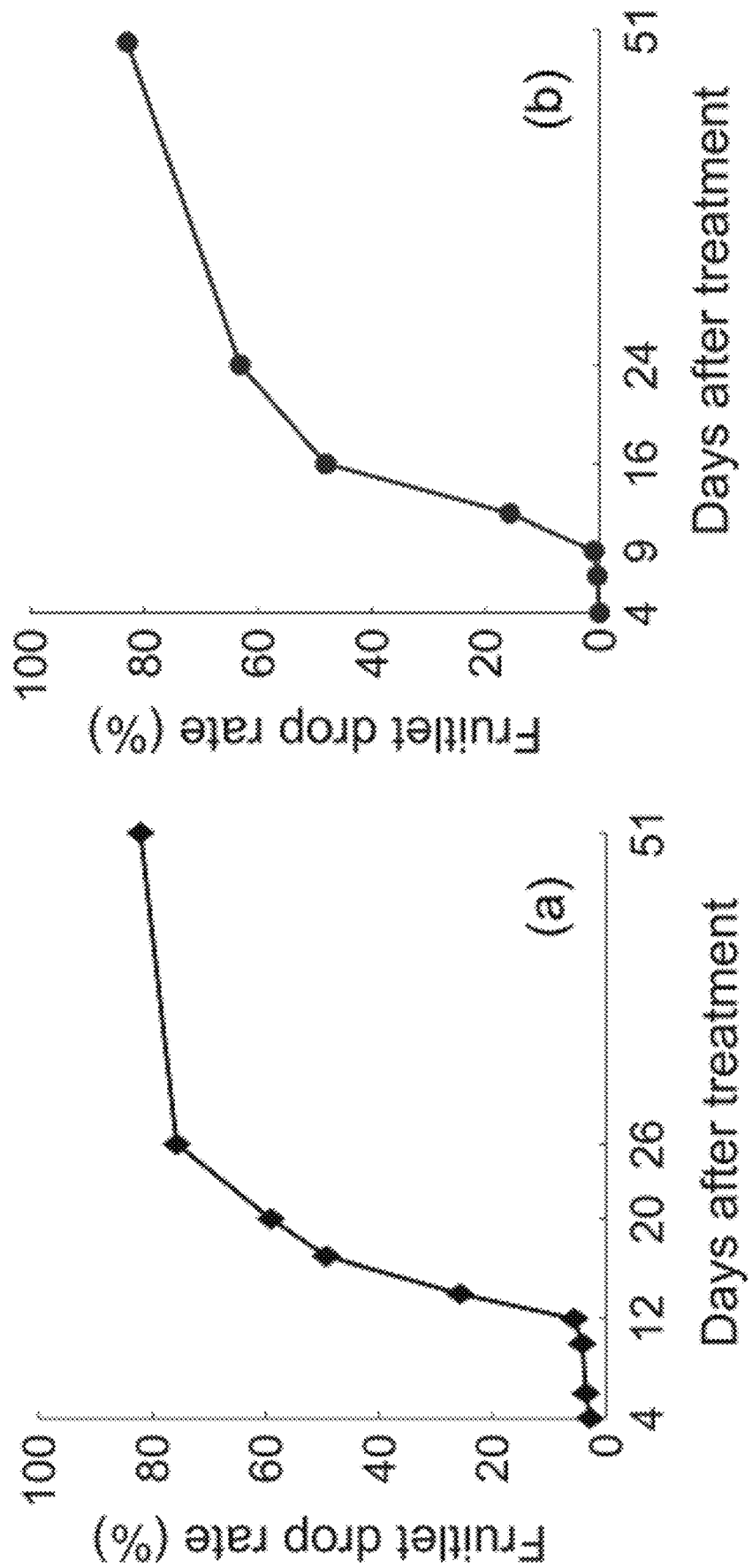
FIGS. 11A-11B show fruitlet drop rates in apples.

FIG. 11A shows the fruitlet drop rate in 'golden delicious' trees treated with synthetic auxins in 2017 (the diamond symbol) (King and two laterals L2, Section 2.1), and FIG. 11B in 2018 (the "o" symbol) (King, L3, and two laterals L2, Section 2.1). In 2017, spectral measurements at 6, 10 and 12 DAT were used to forecast fruitlet drop by 20 or 26 DAT. In 2018, spectral measurements at 4, 7 and 9 DAT were used to forecast fruitlet drop by 24 DAT.

Data Analysis

Figure 12:
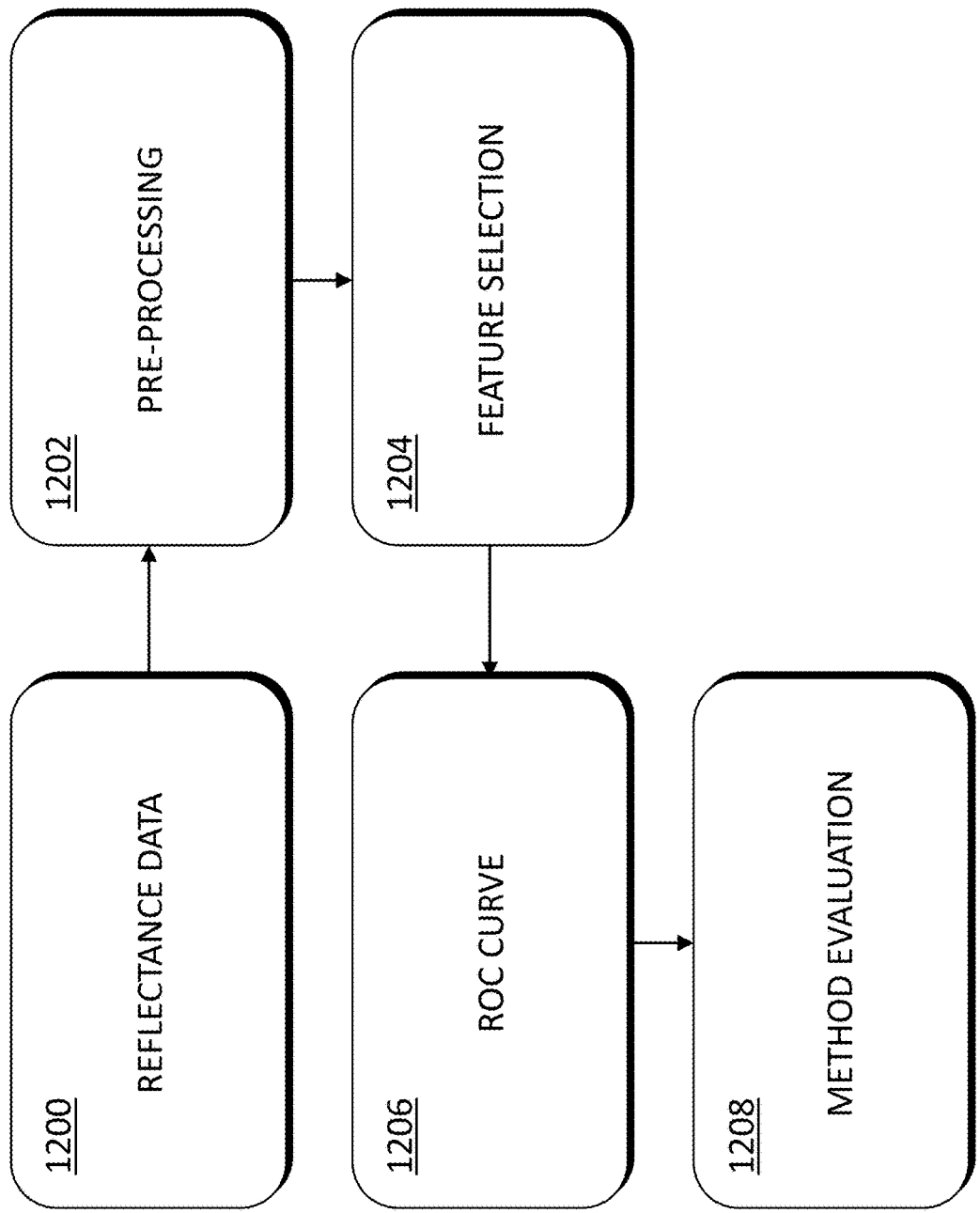
FIG. 12 is a flowchart of data processing steps, in accordance with some embodiments of the present disclosure.

Reference is made to FIG. 12 showing a flowchart of the data processing according to the present disclosure.

In some embodiments, at step 1200, reflectance data may be acquired from a plurality of fruitlet samples, and fruitlet reflectance is calculated according to Eq. (1) above.

In some embodiments, at step 1202, a preprocessing step may be performed with respect to In some embodiments, at a first pre-processing step, sunlight effect correction may be handled as described with reference to Eq. (1) above. In some embodiments, a second preprocessing step may be a Savitsky-Golay filtering of order 2 and window size 25. In some embodiments, a further preprocessing step may be to reduce the original spectral resolution to 9.2 nm (20 data points) or 18.4 nm (40 data points) by computing the average reflectance in each respective window (binning). This decision was based on the fact that a high correlation typically exists between adjacent wavebands and such bands can be combined without substantial information loss. Also, binning decreases computation times and noise. The influence of the binning window size was found to be minimal (details not shown) and therefore only the results obtained with the 9.2 nm window are reported below.

In some embodiments, at a step 1204, a feature selection step may be performed where all combinations of single bands (SB), band differences (BD), and band ratios (BR) in the 400-1000 nm region may be tested as possible features for measurement classification. Band differences and band ratios were assessed as:

$$BD = R_{\lambda_1} - R_{\lambda_2}, \lambda_1 > \lambda_2 \quad (1a)$$

$$BR = R_{\lambda_1} / R_{\lambda_2}, \lambda_1 > \lambda_2 \quad (2a)$$

where $R_\lambda$ denotes the band reflectance, centered at wavelength $\lambda$.

In each case, the optimal threshold value to differentiate between the measurements of dropping and retaining fruitlets was selected via the ROC curve.

In some embodiments, at step 1206, a binary vector was assigned to each measurement according to its status on the reference date: 1 if remained on the tree, 0 if dropped. The ROC curve was built to examine every waveband/waveband pair as a separate classifier. To build the ROC curve itself, different threshold values were tested, plotting true positive rate (sensitivity) vs. false positive rate (1-specificity):

$$\text{Sensitivity} = 100 * TP/(TP+FN) \quad (3a)$$

$$\text{Specificity} = 100 * TN/(TN+FP) \quad (4a)$$

where TP denotes true positive, TN denotes true negative, FP denotes false positive and FN denotes false negative.

Figure 13:
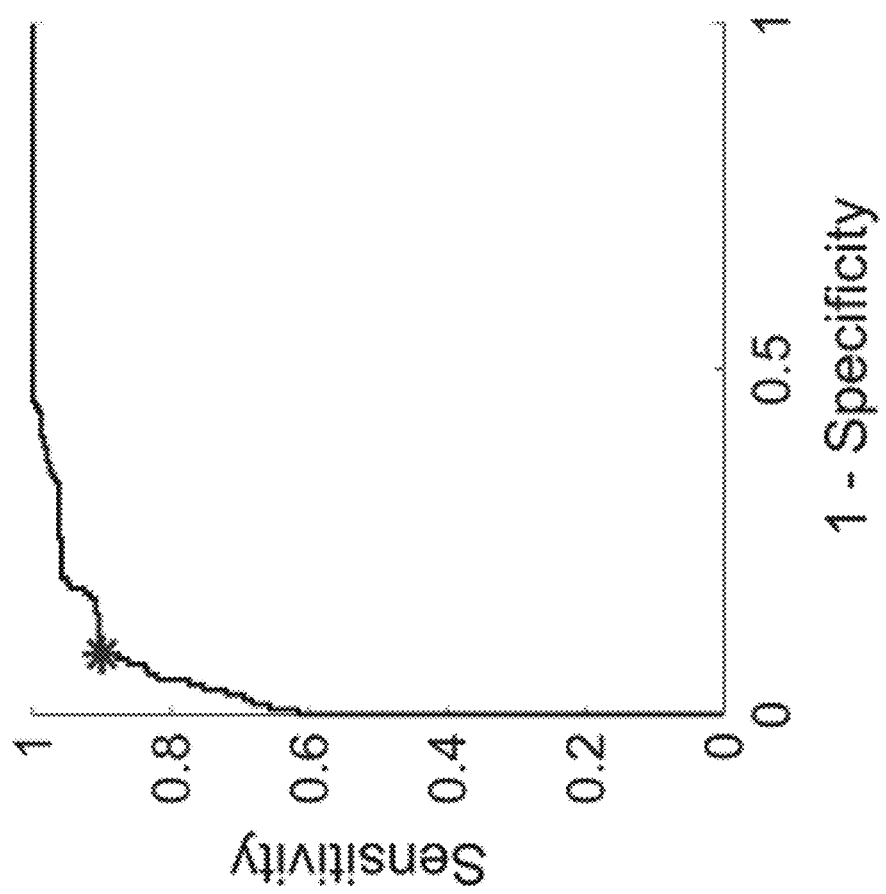

FIG. 13 shows a typical ROC curve obtained using band ratio $R_{693}/R_{674}$ on 9 DAT (2018). The optimal threshold value (marked by "*" in FIG. 3) corresponds to a balance between the high sensitivity and a low (1-specificity) and is determined as the point with the minimal distance to the top left corner. The AUC value is 0.96.

The classification performance of different features in the calibration dataset was evaluated according to the AUC, which does not depend on the threshold value selected. When comparing classifying features, a better feature is characterized by a higher AUC value—the probability that the model ranks a random positive instance higher.

The optimal threshold was determined for each classification feature in the calibration dataset and applied to the validation dataset to determine its performance.

In some embodiments, at step 1208, the model may be evaluated. Between 400 to 623 measurements were performed on the monitoring dates, except on 6 DAT (2017) when only 165 measurements were performed due to technical issues. Internal cross-validation was performed on each day with random data split into 60% calibration and 40% validation datasets, and the results of 100 runs were averaged. All the measurements of a specific fruitlet were always included in the same dataset. Accuracy (Eq. 5a), sensitivity and specificity (Eqs. 3a-4a) were calculated for the validation datasets to assess the model performance.

$$\text{Accuracy} = 100 * (TP+TN)/(TP+TN+FP+FN) \quad (5a)$$

Investigation of The Role of Trichomes

Small-scale measuring campaigns focusing on the role of fruitlets trichomes were conducted in 2018 and 2019 on golden delicious and gala trees, respectively. The 2018 campaign was exploratory and is not reported in detail below. In 2019, twenty fruitlets were tagged on five trees nine days after full bloom, selecting exclusively fruitlets of small (4.7±0.3 mm) and larger (8.7±0.5 mm) diameter on the same tree. Four reflectance measurements were performed on the equatorial region of each intact fruitlet, its trichome layer was gently removed by rubbing with an optical cloth, and four additional measurements were performed on the denuded fruitlet. Additionally, 30 fruitlets were detached from the trees, transferred to the laboratory on ice and in the dark, and imaged with a microscope.

Absorption Coefficients Modeling

The apparent absorption coefficients of intact and denuded fruitlets were estimated from their reflectance spectra, using a procedure inspired by the well-established modeling suggested by Gitelson, Viña, Solovchenko, Arkebauer, and Inoue (2019). Gitelson et al. (2019) used the Kubelka-Munk theory (Kubelka and Munk, 1931) for a medium of infinite thickness with several additional assumptions to retrieve the canopy absorption coefficient from diffuse reflectance measurements. Earlier, the aforementioned modeling was used to propose spectral indexes for pigment content estimation in leaves (Gitelson, Gritz, Merzlyak, 2003; Gitelson & Merzlyak, 2004) and mature apples (Merzlyak, Solovchenko, Gitelson, 2003).

Scattering and absorption properties of a weak-absorbing medium, such as fruit, can be suitably modeled according to Kubelka-Munk theory (Budiastra, Ikeda, Nishizu, 1998; Merzlyak & Chivkunova, 2000). The theory leads to a simple solution for reflectance when the sample has an infinite thickness ($R_{inf}$) relating the optical properties to the following remission function:

$$f(R_{inf}) = (1-R_{inf})^2/2R_{inf} = \alpha/\beta \quad (6a)$$

where $\alpha$ and $\beta$ are the Kubelka-Munk absorption and scattering coefficients respectively.

Since there were measured the reflectance of the whole fruitlet with diameter >4 mm, it can be assumed that transmittance through such a "thick" medium is negligible so that we actually measured $R_{inf}$. This assumption is additionally supported by the findings of Lammertyn, Peirs, De Baerdemaeker, and Nicolai (2000) who reported that the depth of light penetration into a mature apple tissue ranges from 2 to 4 mm at the most.

It can be easily verified that, for values of $R_{inf}^{-1}$ larger than ~2, the relationship in Eq. (6a) corresponds to an almost linear relationship between $R_{inf}^{-1}$ and the remission function $f(R_{inf})$. Indeed, in our experimental data of intact and denuded fruitlets, we found a correlation $R^b$>0.99 between the remission function and reciprocal reflectance (not shown). Replacing $f(R_{inf})$ by $R_{inf}^{-1}$ in (7) yields:

$$R_{inf}^{-1} = \alpha/\beta = (\alpha_p + \alpha_0)/\beta \quad (7a)$$

where $\alpha_p$ and $\alpha_0$ are absorption coefficients of "pigments of interest" and "interfering pigments" as suggested in Gitelson et al. (2019).

The potential influence of brown "interfering" pigments that absorb in the NIR range and/or losses due to the apparent absorption can be reduced by subtracting the reciprocal reflectance in the NIR range (760-800 nm), (denoted $R_{NIR}^{-1}$), leading to:

$$R_{inf}^{-1} - R_{NIR}^{-1} \propto \alpha_p/\beta \quad (8a)$$

The scattering coefficient $\beta$ can be approximated by $R_{NIR}$ in order to estimate the apparent absorption coefficient of pigments:

$$\alpha_p \propto R_{NIR}(R_{inf}^{-1} - R_{NIR}^{-1}) = R_{NIR}/R_{inf} - 1 \quad (9a)$$

It was proved empirically that Equation 9a is suitable for the estimation of pigment content of leaves and mature apples with high $R^2$ values reported (0.88-0.96). Strong correlations ($R^2$=0.8-0.9) were also found between the values of the absorption coefficient at 670-675 nm estimated by the Equation 9a and chlorophyll content in mature apples and canopy. Furthermore, the absorption and reduced (transport) scattering coefficients in the 500-1000 nm spectral range were estimated for various fruits and vegetables (including apples, peach, and kiwifruit) using the diffusion theory model. The relationship between the Kubelka-Munk scattering coefficient and the transport coefficients is described by:

$$\beta = (3\mu'_s - \mu_\alpha)/4 \quad (10a)$$

where $\mu_\alpha$ and $\mu'_s$ are the absorption and scattering transport coefficients.

In Qin & Lu (2008) the reduced scattering coefficient $\mu'_s$ was at least one order of magnitude higher than the absorption transport coefficient $\mu_\alpha$, which supports the assumption of a highly scattering medium. The reduced scattering coefficient did not exhibit any particular spectral features but rather showed a slightly decreasing trend with wavelength increase (FIG. 7 in Qin & Lu (2008)). In such a case, the Kubelka-Munk scattering coefficient $\beta$ can be approximated as $3\mu'_s/4$ and substituted by $R_{NIR}$, as was suggested by Gitelson et al. (2019).

It must be noted that not all the literature supports the above assumptions. Budiastra and Ikeda (1998) reported contradictory results on Kubelka-Munk scattering coefficients for mature apples and pears computed from the measurements of the reflectance and transmittance of thin fruit slices (Kubelka-Munk theory solutions for semi-infinite medium thickness). The reported scattering coefficients showed more pronounced variations in the spectral ranges of strong pigment absorption. The fact that Budiastra and Ikeda (1998) used measurements of thin sample slices, which may have affected the spectral measurements, may be responsible for the apparent discrepancies. For this reason, we opted to follow the approach supported by Gitelson et al. (2019) and Qin and Lu (2008) and assumed that approximation of the Kubelka-Munk scattering coefficient $\beta$ by $R_{NIR}$ is valid for the evaluation of the apparent absorption coefficient in both intact and denuded apple fruitlets.

Microscope Imaging

Surfaces of 30 intact fruitlets of a small diameter (4-5 mm) and significantly larger diameter (8-9 mm) were imaged to highlight differences in trichome density using an Axioskop 40 microscope (Carl Zeiss, Jena, Germany) equipped with a ×5 magnification objective and an AxioCam ICc 3 camera. Prior to imaging, the fruitlets were kept for ~0.5 hours at room temperature. Each image was composed of a stack of 10-15 images taken with manual focus adjustment to overcome blurring due to a fruitlet curvature. ZEN 2 blue edition (Carl Zeiss, Jena, Germany) software was used for the imaging and the Z-Stack feature was used for combining the images.

Results and Discussion

Waveband Selection by the ROC Curve

Figure 14:
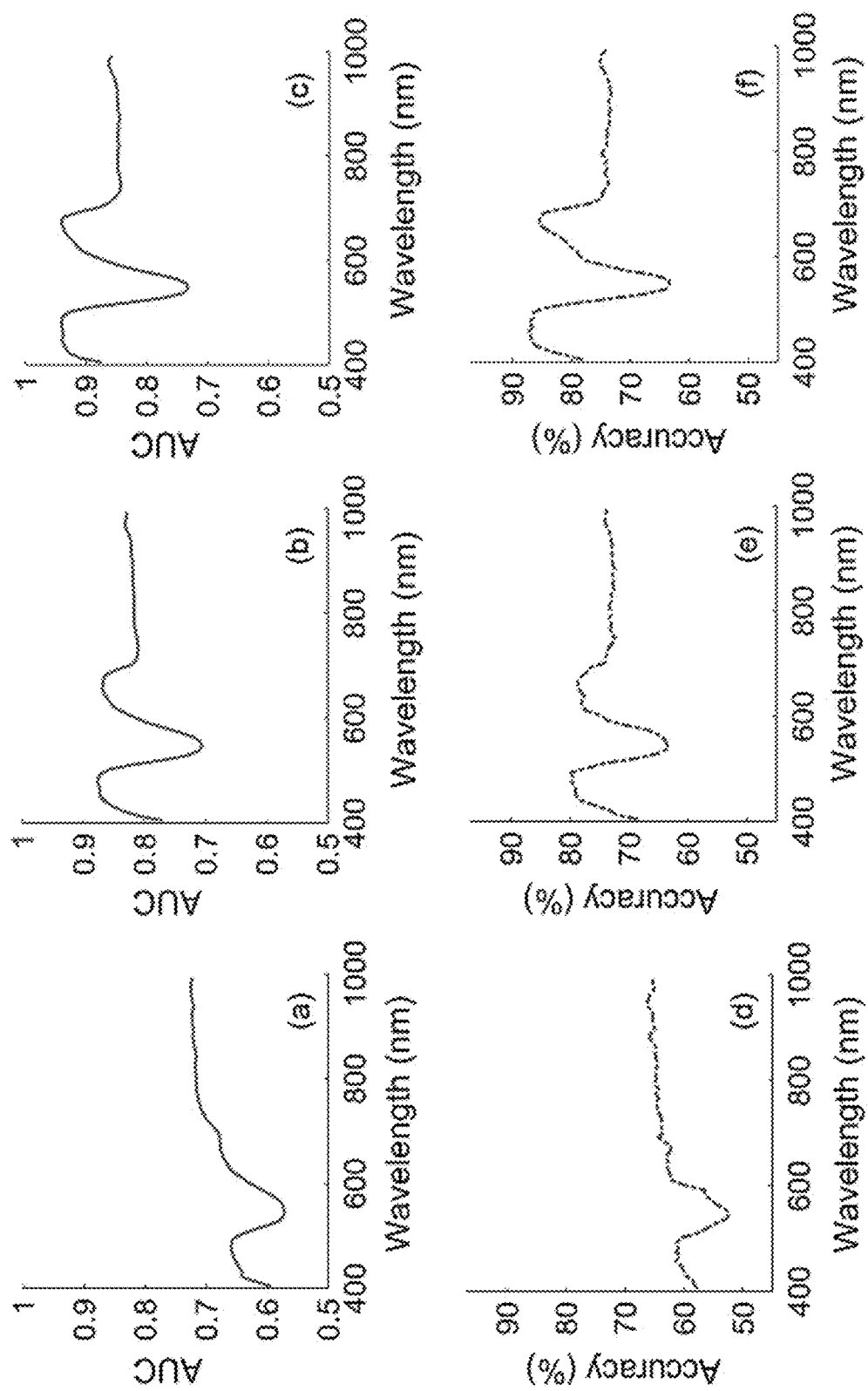

FIG. 14 shows AUC and classification performance for single-band reflectance thresholding. The results of the measurements conducted on 4, 7 and 9 DAT (2018) are presented as an example. The AUC for the calibration datasets (panels a-c) (solid lines) (60% of the data) and corresponding classification accuracy for the validation datasets (d-f) (dash-dotted lines) (40% of the data) for spectral band thresholding at 4 DAT (panels a, d); 7 DAT (panels b, e) and 9 DAT (panels c, f).

According to the AUC graphs in FIG. 14 (panels b and c), the optimal spectral bands for reflectance thresholding of 7 or 9 DAT measurements (2018) were located in the blue (440-500 nm) and red regions (640-690 nm) of the spectrum with a small advantage for the blue range. The accuracy of the classification in the validation datasets (FIG. 14, panels e and f) was optimal in the aforementioned regions. The blue and red reflectance in the visible spectrum is usually associated with chlorophyll absorption. On the other hand, the NIR spectral band thresholding seemed preferable for 4 DAT measurements (FIG. 14, panels a and d).

Comparing the maximal AUC values and corresponding classification accuracies for the three dates, the highest AUC values and accuracies were obtained when using 9 DAT measurements (FIG. 14, panels c and f). This result is not surprising since it is reasonable to expect that the differences between fruitlets destined to drop and retain become more pronounced with fruitlet development. The results obtained using measurements at 6, 10 and 12 DAT (2017) showed the same trends: thresholding in the blue and red spectral regions was preferable at 10 and 12 DAT and thresholding in the NIR was preferable at 6 DAT, regardless of the reference date (20 or 26 DAT) (details not shown).

The obvious differences observed between the results obtained using 4-6 DAT measurements vs. later measurements led us to conduct further analyses separately for these two groups of measurements.

Figure 15:
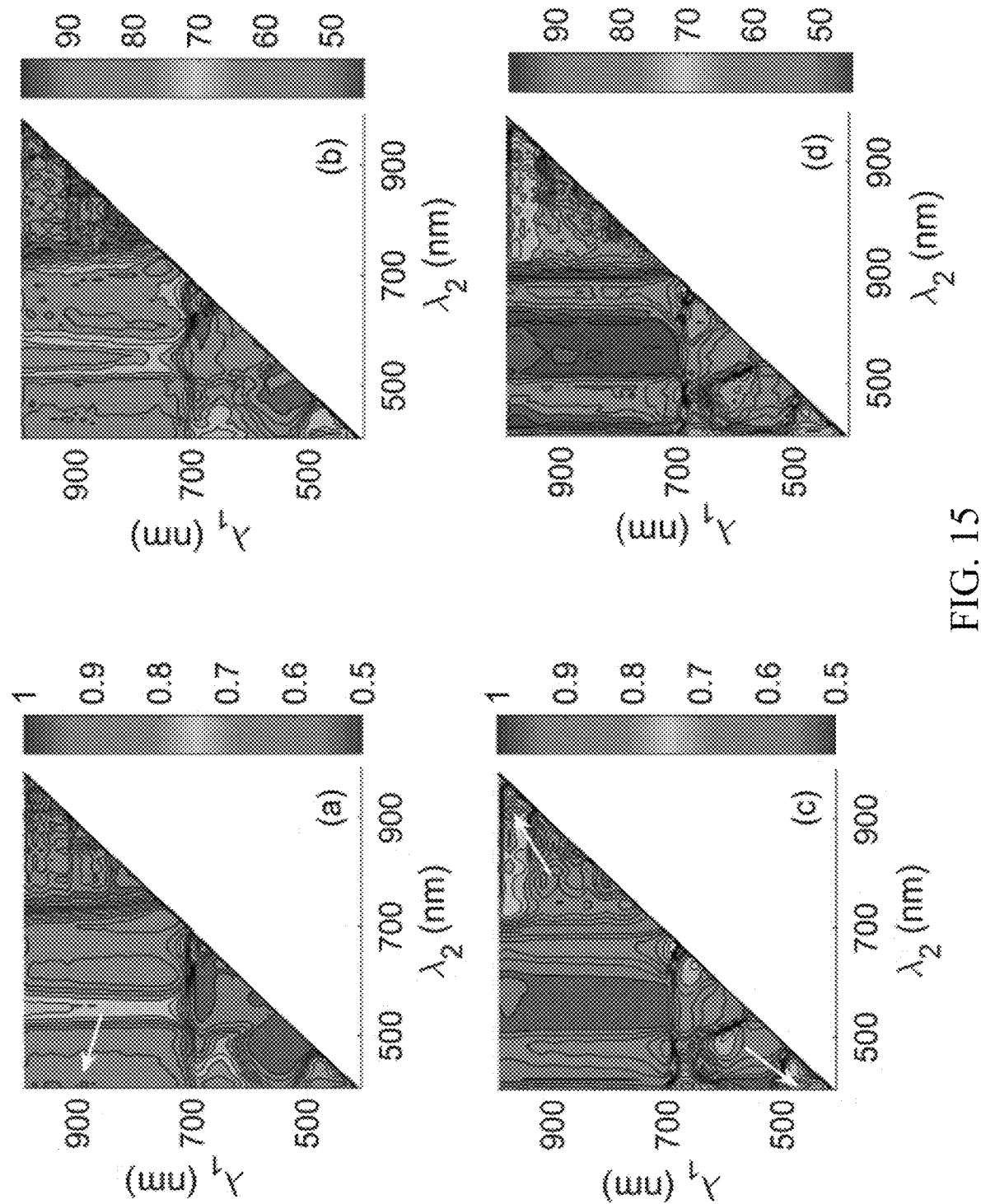

FIG. 15 shows AUC contour plots for the calibration datasets and the corresponding classification accuracy for the validation datasets for all possible band differences (Equation 1a) and band ratios (Equation 2a) using the measurements at 6 DAT (2017, with the reference date 20 DAT). Lower AUC values and accuracies were obtained with the second reference date (26 DAT) due to a longer lead-time. However, the band difference performance was similar in terms of the optimal regions (not shown). Contour plots of AUC values for the calibration datasets (panels a, c) (60% of the data) and classification accuracies for the validation datasets (panels b, d) (40% of the data) for band difference thresholding (a, b) and band ratio thresholding (panels c, d) at 6 DAT (2017, reference date 20 DAT). White arrows indicate regions with the highest AUC values.

According to the AUC contour plot at 6 DAT (FIG. 15a), the best band difference thresholding options were obtained after subtracting the reflectance in the blue range (404 ... 475 nm) from reflectance in the NIR range (757 ... 974 nm) (red region marked by arrow). It is noteworthy that the spectral regions corresponding to maximal AUC values (0.94-0.95) were quite large, indicating certain flexibility in band selection. Comparing the contour plots of the AUC values (FIG. 15, panel a) with the contour plots of the classification accuracies (FIG. 1, panel b) showed that the regions associated with higher AUC corresponded to better validation accuracies. This result supported the selection of AUC as an appropriate property for classifier performance assessment.

The performance of the best band ratio thresholding at 6 DAT (FIG. 15, panel c) was poor with lower AUC values (0.84-0.85), which were obtained only at very narrow wavelength ranges, namely $\lambda_1$=974 ... 983 nm and $\lambda_2$=907 ... 926 nm=466 ... 484 nm and $\lambda_2$=404 ... 413 nm (yellow regions marked by white arrows).

Figure 16:
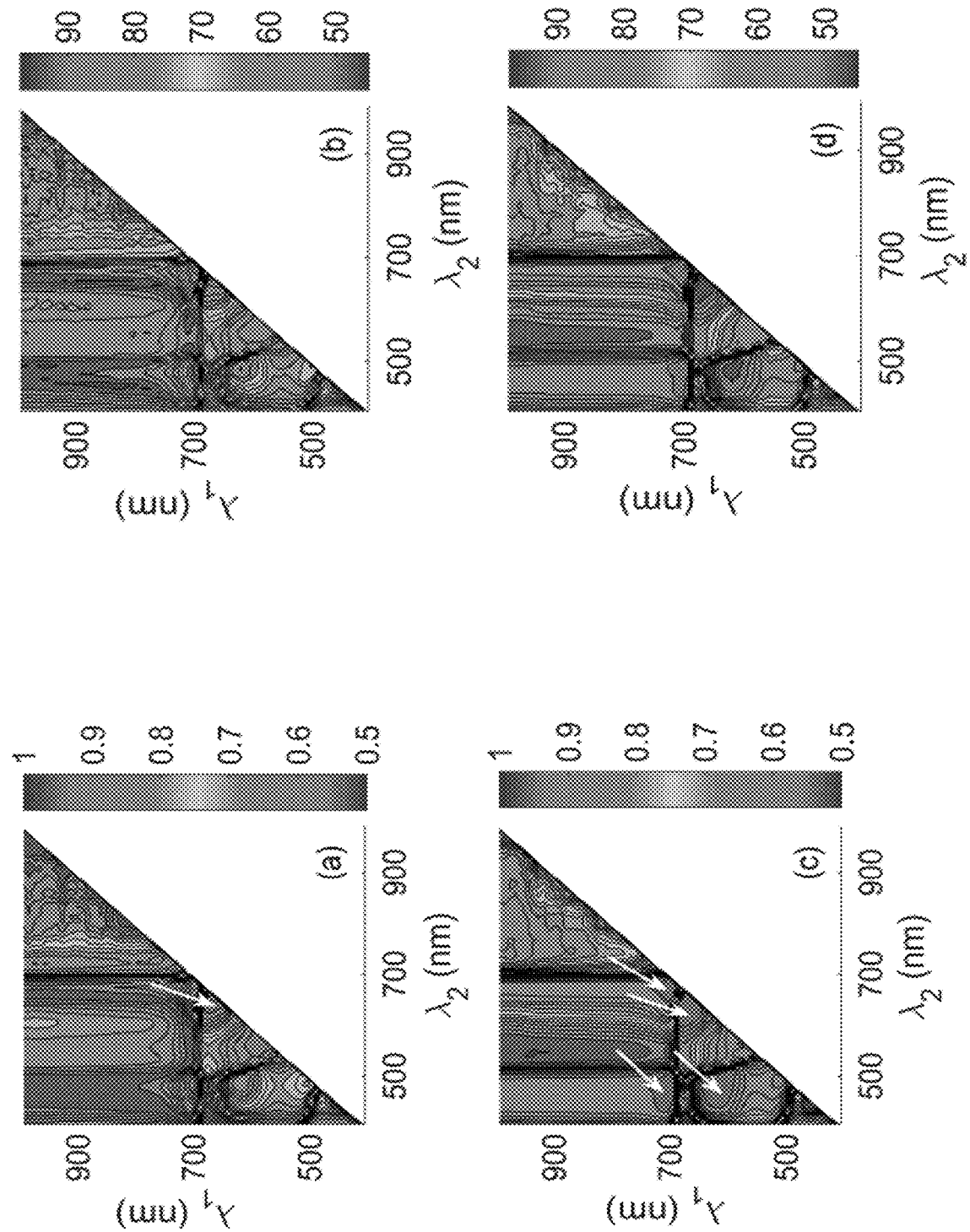

FIG. 16 shows AUC contour plots for the calibration datasets and the corresponding classification accuracies for the validation datasets for all possible band differences (Equation 1a) and band ratios (Equation 2a) using the measurements at 10 DAT (2017, with reference date at 20 DAT). Again, slightly lower AUC values and lower accuracies were obtained with the second reference date (26 DAT) due to a longer lead-time. However, the band difference performance was similar in terms of optimal regions (not shown). Contour plots of AUC values for the calibration datasets (panels a, c) (60% of the data) and classification accuracies for the validation datasets (panels b, d) (40% of the data) for band difference thresholding (panels a, b) and band ratio thresholding (panels c, d) at 10 DAT (2017, reference date 20 DAT). White arrows indicate regions with the highest AUC values.

FIG. 16, panels a and c indicate that band ranges with high AUC values (dark red regions marked by arrows, AUC>0.96) could be selected at 10 DAT for both the band difference and ratio thresholding. However many more good options exist for the ratio thresholding (dark red regions marked by white arrows in FIG. 16, panel c), for instance when the red-edge or near red-edge reflectance ($\lambda_1$= 693 ... 720 nm) is divided by the reflectance in the blue ($\lambda_2$=440 ... 493 nm) or red ($\lambda_2$=665 ... 683 nm) spectral range or the ratio of two wavelengths in the red range ($\lambda_1$=656 ... 683 and $\lambda_2$=610 ... 647 nm). For band difference thresholding, only one narrow spectral range was suitable (dark red region in FIG. 16, panel a, namely $\lambda_1$= 665 ... 674 nm and $\lambda_2$=638 ... 647). Therefore, band ratio thresholding seems preferable for that date. Again, comparing the contour plots of the AUC values (FIG. 1, panels a and c) with the contour plots of the classification accuracies (FIG. 16, panels b and d) confirmed that better validation accuracies correspond to wavebands combinations with higher AUC values.

The most obvious observation is that much higher accuracies were achieved at 10 DAT than at, 6 DAT due to the shorter lead-time (10 days forecast vs. 14 days forecast). Another obvious observation is the better performance of band difference thresholding at 6 DAT (with $\lambda_1$=757 ... 974 nm and $\lambda_2$=404 ... 475 nm) and band ratio thresholding at DAT (for example $\lambda_1$=702 ... 720 nm and $\lambda_2$=440 ... 493 nm or $\lambda_1$=693 ... 720 nm and $\lambda_2$=665 ... 683 nm. Band difference thresholding with the NIR and blue spectral ranges was optimal at 4 DAT (2018) as well, while ratio thresholding utilizing the wavebands at the red-edge, red or blue spectral ranges was optimal at 12 DAT (2017) and 7-9 DAT (2018) (details not shown).

As was previously mentioned for the single-band thresholding, further analyses were conducted separately for the measurements at 4-6 DAT (using band difference thresholding), and the measurements at 7-12 DAT (using band ratio thresholding). Table 1a summarizes the optimal band difference combinations for 4-6 DAT based on the calibration datasets. The spectral ranges listed in the Table correspond to spectral combinations that resulted in AUC values which were within 3% of the maximum AUC value.

TABLE 1a

Optimal bands for band difference thresholding at 4-6 days after treatment (DAT) according to the calibration datasets. The binning window is 9.2 nm.

| | Measurement date (DAT) | Reference date (DAT) | Year |
|---|---|---|---|
| Dates selected | 6 | 20 | 2017 |
| | 6 | 26 | 2017 |
| | 4 | 24 | 2017 |
| Optimal bands >0.97 max(AUC) | $R_{860\ldots983} - R_{404}$; $R_{898} - R_{413}$; $R_{907\ldots926} - R_{413}$; $R_{945\ldots993} - R_{413}$; $R_{983} - R_{422}$; | | |

Twenty-five options of band differences were identified for 4-6 DAT measurements when selecting AUC values within 3% of the maximum AUC value (Table 1a). All these corresponded to differences between reflectance in the NIR and blue spectral ranges.

Table 2a summarizes the optimal band ratio combinations for 7-12 DAT according to the calibration datasets. The spectral ranges listed in the Table correspond to spectral combinations that resulted in AUC values which were within 5% of the maximum AUC value.

TABLE 2a

Optimal bands for band ratio thresholding at 7-12 days after treatment (DAT) according to the calibration datasets. The binning window is 9.2 nm.

|  | Measurement date (DAT) | Reference date (DAT) | Year |
|---|---|---|---|
| Dates selected | 10 | 20 | 2017 |
|  | 10 | 26 | 2017 |
|  | 12 | 20 | 2017 |
|  | 12 | 26 | 2017 |
|  | 7 | 24 | 2018 |
|  | 9 | 24 | 2018 |
| Optimal bands >0.95 max(AUC) | $R_{693\ldots683}/R_{674}$; $R_{693}/R_{665}$; $R_{702}/R_{674\ldots683}$; $R_{711\ldots720}/R_{475}$; $R_{711}/R_{484\ldots493}$; | | |

As can be seen from Table 2a, nine options of band differences were identified for 7-12 DAT when retaining combinations for which the AUC was within 5% of the maximum AUC value. All these corresponded to ratios of reflectance near the red-edge of the spectrum (693 . . . 720 nm) and reflectance in the red or blue spectral ranges.

Table 3a and Table 4a further detail the classification performance of one combination for each case, namely $R_{973}$-$R_{404}$ at 4-6 DAT and of $R_{693}/R_{674}$ at 7-12 DAT, respectively.

TABLE 3a

AUC in calibration datasets, optimal threshold values and classification performance for validation datasets, based on band difference $R_{973}$ − $R_{404}$ when using 4 or 6 days after treatment (DAT) measurements.

|  | Year | |
|---|---|---|
|  | 2017 | 2018 |
| Reference date (DAT) | 20 | 26 | 24 |
| Measurement date (DAT) | 6 | 6 | 4 |
| AUC | 0.96 | 0.91 | 0.75 |
| Optimal threshold | 23 | 22.6 | 25.4 |
| Accuracy (%) | 87 | 84 | 66 |
| Sensitivity (%) | 84 | 87 | 71 |
| Specificity (%) | 88 | 83 | 63 |

TABLE 4a

AUC in calibration datasets, optimal threshold values and classification performance in validation datasets, based on band ratio $R_{693}/R_{674}$ when using 7-12 days after treatment (DAT) measurements.

| Year | | | | | |
|---|---|---|---|---|---|
| 2017 | | | | 2018 | |
| Reference date (DAT) | | | | | |
| 20 | | 26 | | 24 | |
| Measurement date (DAT) | | | | | |
| 10 | 12 | 10 | 12 | 7 | 9 |
| AUC 0.98 | 0.97 | 0.87 | 0.82 | 0.85 | 0.96 |
| Optimal threshold 1.36 | 1.42 | 1.39 | 1.45 | 1.28 | 1.31 |
| Accuracy (%) 95 | 94 | 78 | 78 | 76 | 90 |

TABLE 4a-continued

AUC in calibration datasets, optimal threshold values and classification performance in validation datasets, based on band ratio $R_{693}/R_{674}$ when using 7-12 days after treatment (DAT) measurements.

| Year | | | | | |
|---|---|---|---|---|---|
| 2017 | | | | 2018 | |
| Reference date (DAT) | | | | | |
| 20 | | 26 | | 24 | |
| Measurement date (DAT) | | | | | |
| 10 | 12 | 10 | 12 | 7 | 9 |
| Sensitivity (%) 97 | 94 | 86 | 89 | 76 | 89 |
| Specificity (%) 95 | 94 | 76 | 74 | 76 | 90 |

It can be seen from Tables 3a and 4a that the accuracies for fruitlet classification with $R_{973}$-$R_{404}$ at 4-6 DAT ranged from 66% to 87%, while the accuracies for fruitlet classification with $R_{693}/R_{674}$ at 7-12 DAT ranged from 76% to 95%. Higher accuracies were often obtained for the later monitoring dates (9-12 DAT) and/or shorter forecast lead-times (8-15 days). The poorer results on 4 DAT can be explained not only by the fact that the influence of the thinner application was less pronounced but also by the fact that the measurement at 4 DAT was much more complex due to fruitlet sepals' contribution and the overall very small size of the fruitlet (age of 7 days).

Sensitivity values were generally above 80% (Tables 3a and 4a), which is considered "good" (Luo et al., 2012), and dropped below this value at 4 DAT and 7 DAT (2018) when longer forecast lead-times (17-20 days) were selected. A similar trend was observed for the specificity, which however also dropped below 80% also at 10 and 12 DAT with shorter forecast lead-times (14-16 days). The fraction of false-positives at the corresponding dates was high, meaning that certain fruitlets, which were still developing normally at the measurements date eventually dropped.

Looking into the optimal thresholds values (Table 3a) for BD=$R_{973}$−$R_{404}$, a notably higher threshold value (25.4%) was selected at 4 DAT, compared to 6 DAT. This could be due to the higher drop in reflectance values in the NIR range between the dates, compared to the change in the blue range (not shown). The optimal threshold values for BR=$R_{693}/R_{674}$ were 1.28-1.45, generally increasing with fruitlet age. This is not surprising, since fruitlet development at the beginning of the season is a very dynamic process, and there were noticeable differences between the measurements performed on normally-developing fruitlets several days apart.

Intact and Denuded Fruitlet Surfaces

Figure 17B:
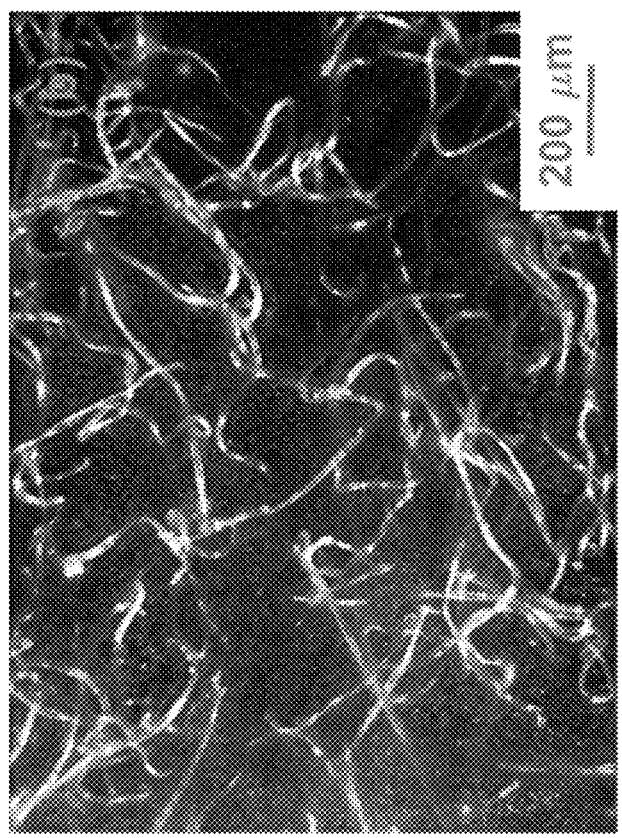
Figure 17A:
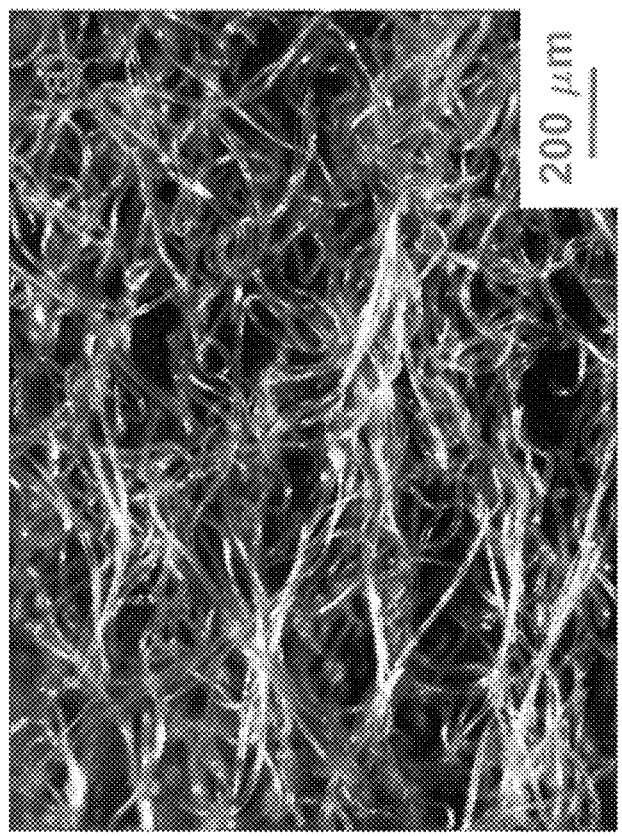

This section reports the complimentary analysis that was conducted in order to gain some insight into the causes of the observed spectral differences. It is well known that apple fruitlets are initially covered by non-grandular trichomes. Qualitatively it looks like the number of trichomes remains fairly constant during fruitlet development, causing a decrease in trichome density. It must be noted that such a phenomenon was observed in two different apple varieties—golden delicious and gala in 2018 and 2019 respectively. The inspection of fruitlets at different developmental stages (i.e. difference sizes) picked on the same date and from the same tree confirmed our assumption. The decrease in trichomes density can be appreciated in FIGS. 17A-17B, which show microscope images of the surface of intact fruitlets with diameter 4.3 mm and 9.3 mm, picked on the same date. Typical microscope images of intact fruitlet surfaces. 17A corresponds to a fruitlet with 4.3 mm diameter and 17B corresponds to a fruitlet with 9.3 mm diameter. Both images were constructed by Z-stacking in order to deal with fruitlet curvature. The contrast of the final images was adjusted.

FIG. 17 shows that fruitlet trichomes are tubular, twisted and distributed mainly in a horizontal and not vertical orientation. The average trichome length is ~1 mm while the thickness in the central part is ~12-15 microns (based on observations at higher microscope magnification, not shown). FIG. 17 highlights that the density of the trichome layer on the fruitlet surface is initially very high (17A) and this layer becomes much sparser at the equatorial zone as the fruitlet develops (17B). It must be noted that trichome density on the surface adjacent to fruitlet stamen and pedicel remains significantly higher than on the equatorial zone due to a much lower surface expansion (not shown).

Figures 18A, 18B:
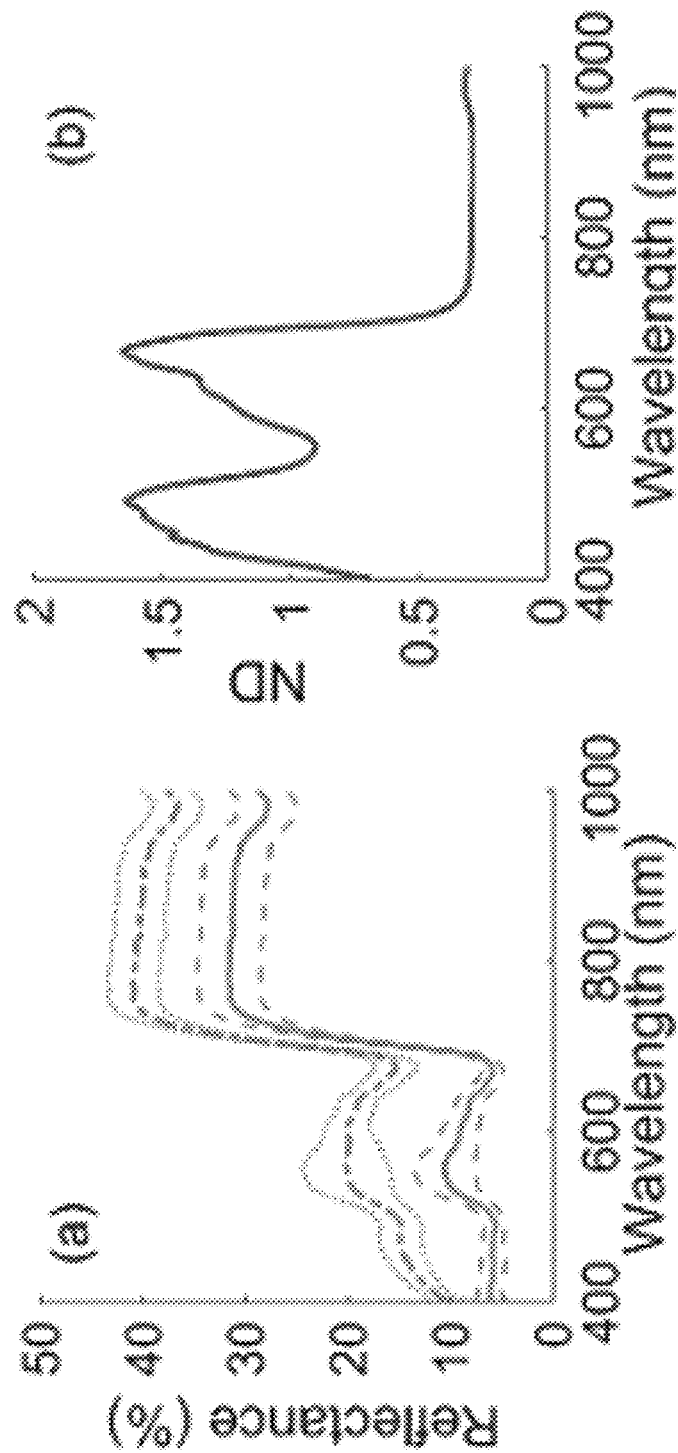
Figures 18C, 18D:
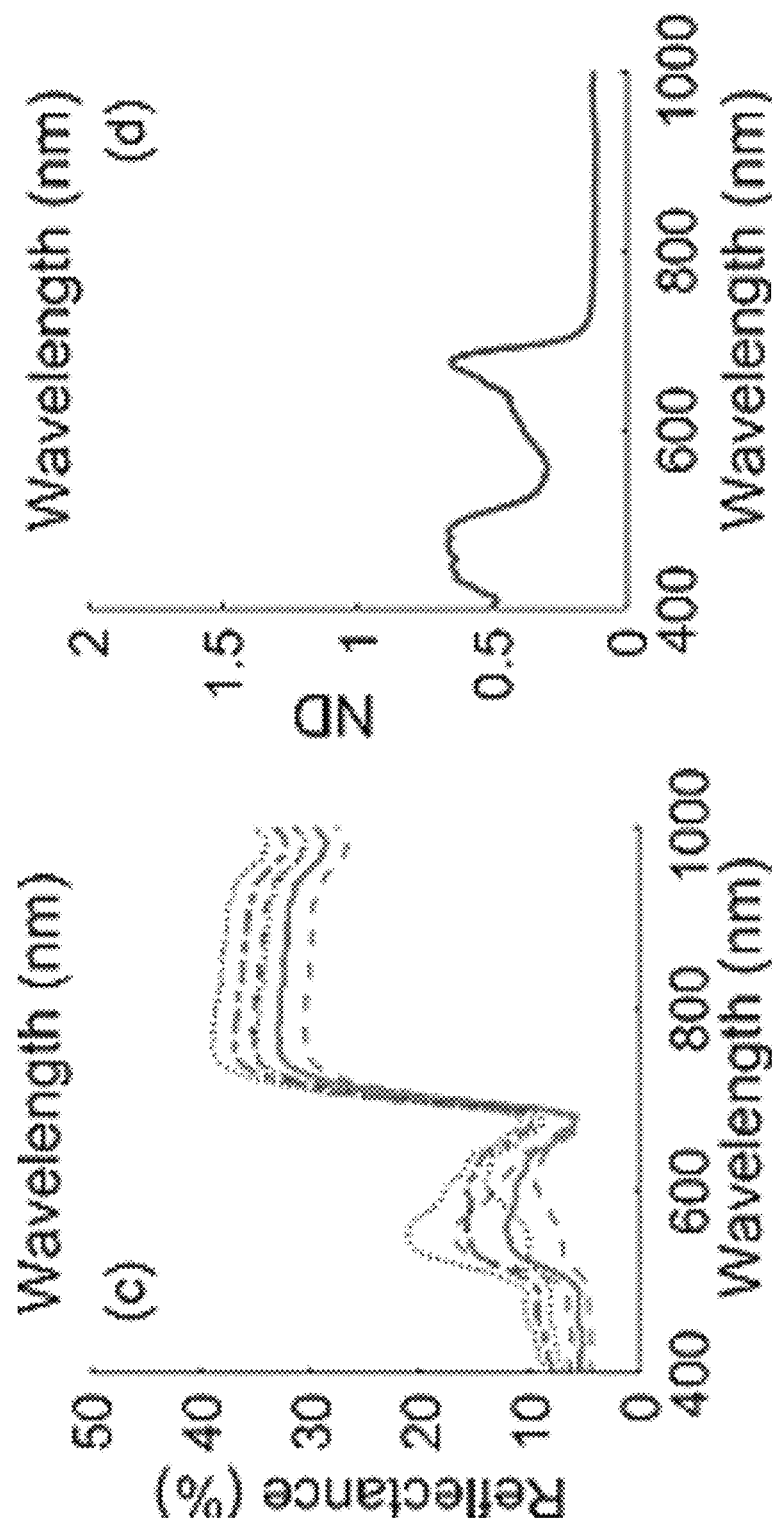

FIGS. 18A and 18C present the average reflectance curves of intact (dash-dotted line) vs. denuded fruitlets (solid line) of two sizes: 4.7±0.3 mm and 8.7±0.5 mm diameter. Additionally, FIGS. 18B and 18D show normalized difference curves, calculated according to the equation:

$$ND=(R_i-R_d)/R_d \quad (11a)$$

where ND is the normalized reflectance difference, and $R_i$ and $R_d$ are the average reflectance of intact and denuded fruitlets respectively.

FIGS. 18: 18A, 18c show mean and mean ±std reflectance curves of intact (dash-dotted lines) and denuded (solid lines) fruitlets with average diameter 4.7±0.3 mm (18A) and 8.7±0.5 mm (18C). Mean±std curves are shown by dotted lines and dashed lines for intact and denuded fruitlets respectively. (18B, 18D): Corresponding normalized mean reflectance difference (ND) (Equation 11a). N=20. (18E): Mean and mean±std reflectance curves of retaining (solid line) and dropping (dash-dotted line) fruitlets. Mean±std curves are shown by the dotted line and dashed line for dropping and retaining fruitlets respectively. (18F): corresponding normalized mean reflectance difference (ND) (Equation 11a). The result of 9 DAT (2018) is shown as an example.

As can be seen from FIGS. 18A and 18C, trichome removal caused a strong decrease in the reflectance in the whole Vis-NIR range in both small and large fruitlets (dash-dotted lines vs. solid lines). The decrease in reflectance was more pronounced for the smaller fruitlets. Regardless of the fruitlets size, trichome removal resulted in more pronounced differences in the red (660-680 nm) and blue (460-500 nm) spectral ranges (FIGS. 18B and 18D).

Figures 18E, 18F:
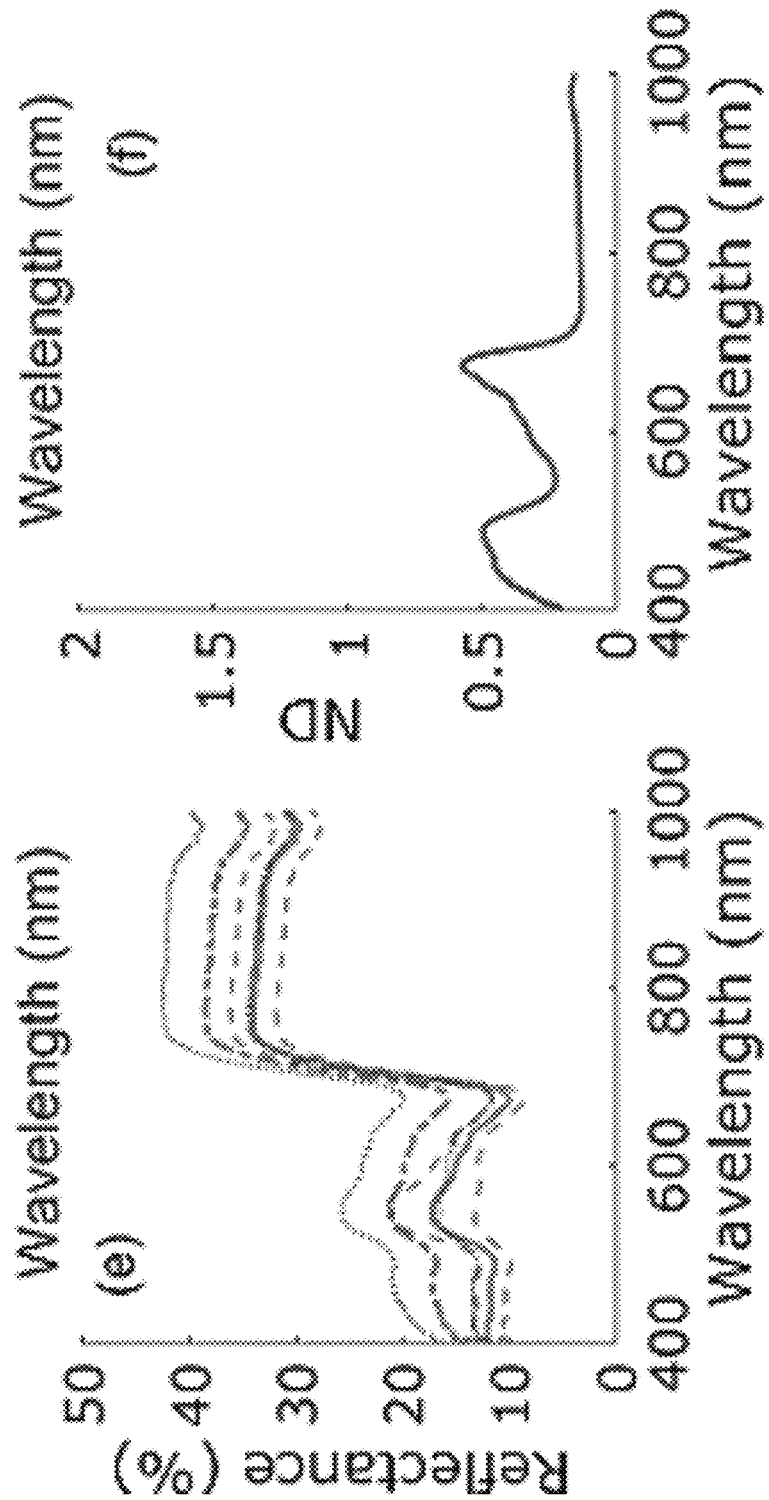

FIGS. 18E and 18F present a typical example of average reflectance curves of dropping (dash-dotted line) and retaining (solid line) fruitlets (FIG. 18A) and their normalized reflectance difference (FIG. 18B), reproduced from Orlova et al. (2020).

The similarity between the intact vs. denuded and dropping vs. retaining fruitlets in FIG. 18 is striking: dropping fruitlets had higher reflectance over the whole Vis-NIR range, and the differences between the curves were more pronounced in the blue and red spectral regions. The similarity between the signals can be explained by the fact that fruitlets that are destined to drop develop more slowly than fruitlets that are destined to remain on the tree so that trichome density remains higher on the former than on the later.

Figures 19A, 19B:
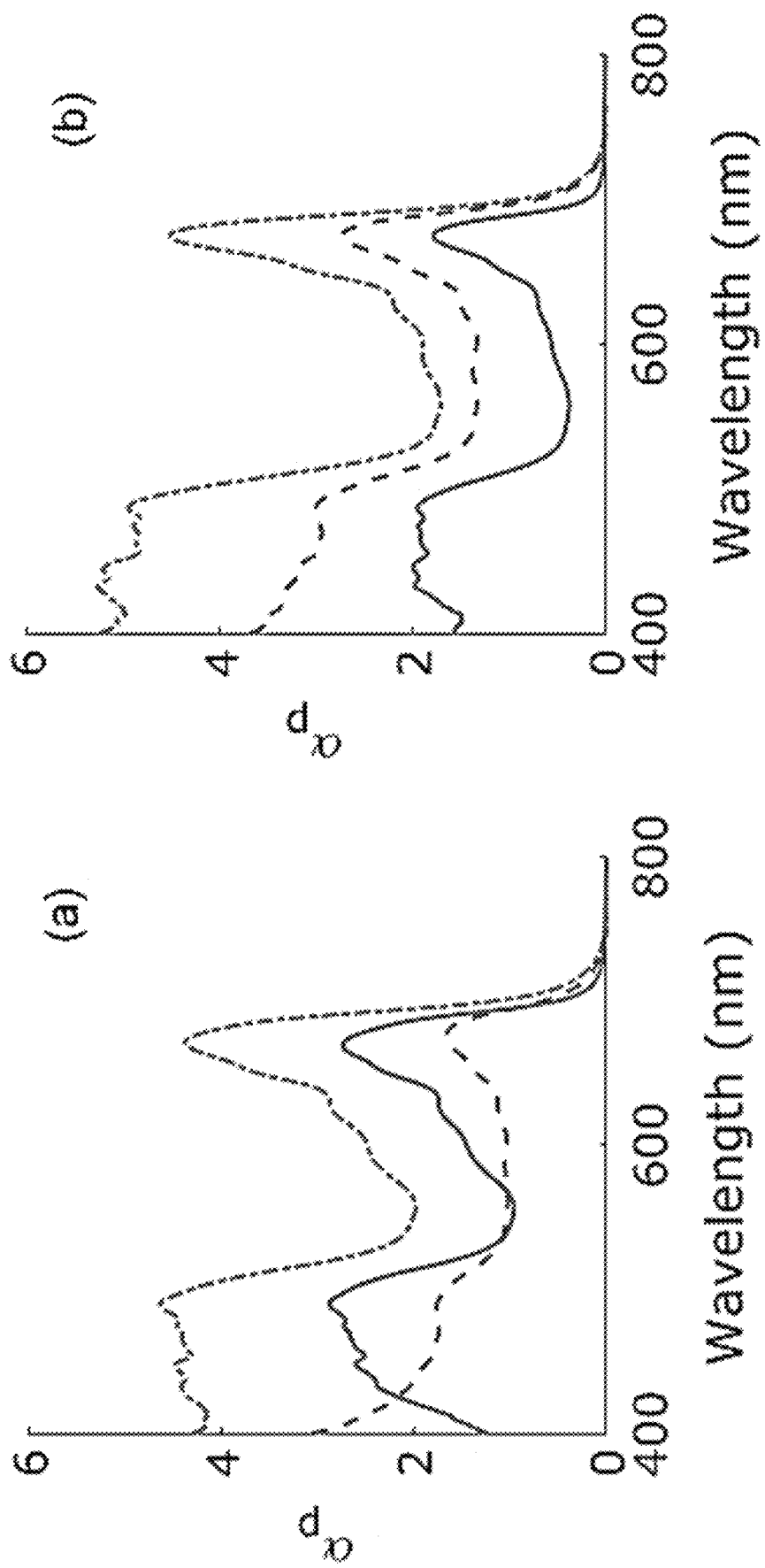
Figure 20B:
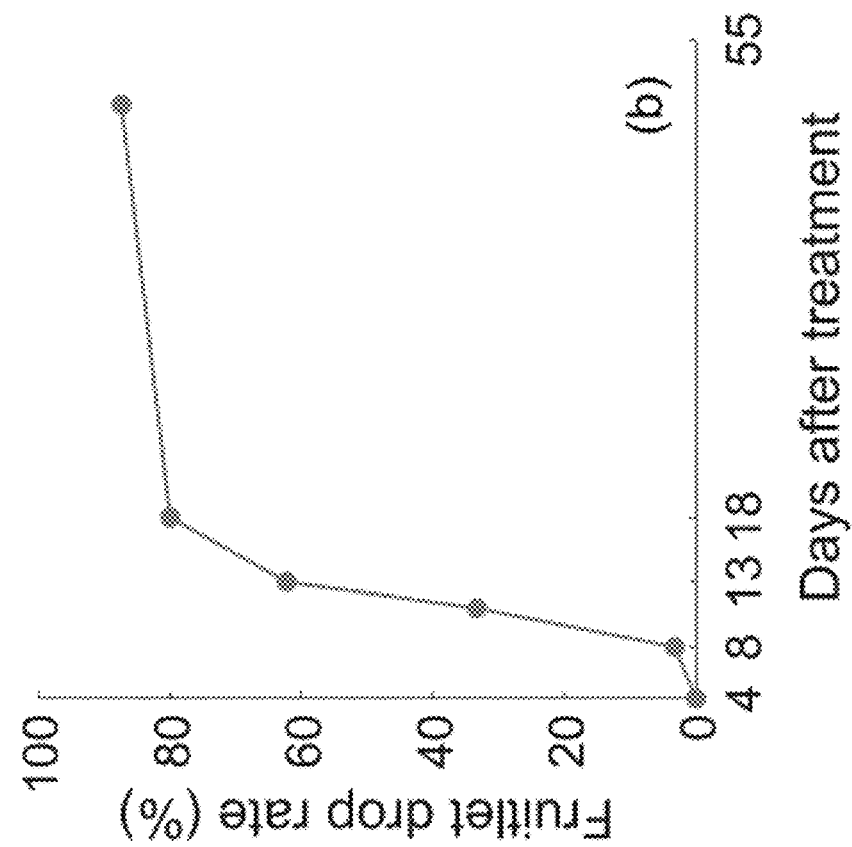
FIGS. 20A-20B fruitlet drop rates in apples.
Figure 20A:
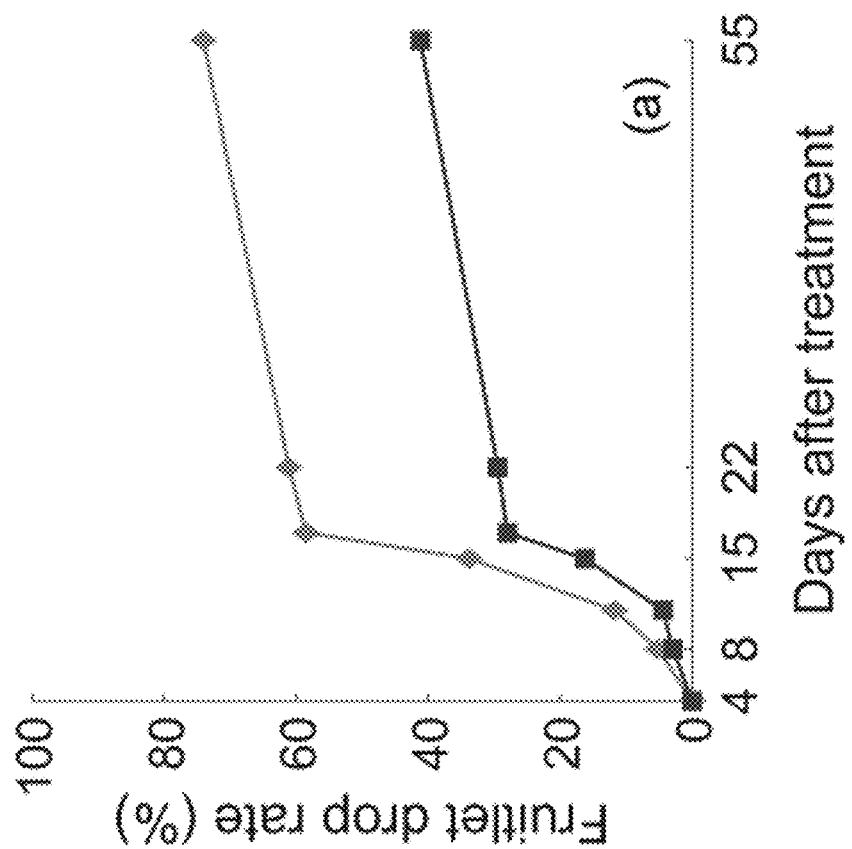

Trichome density influences the contribution of the fruitlet surface and subsurface to the overall reflectance signal. In the next step, the apparent absorption coefficients of intact and denuded fruitlets were evaluated via the well-established model (Gitelson et al., 2019) described in Section 2.4.2 (Equation 9a). The results obtained using reflectance at 800 nm to estimate Ra are shown in FIG. 19. Apparent absorption coefficient ($\alpha_p$, Equation 10a) of intact (dashed lines) and denuded (dash-dotted lines) fruitlets and their differences (solid lines) for fruitlets with diameter of 4.7±0.3 mm (19A) and 8.7±0.5 mm (19B). N=10 for each fruitlet size group.

As can be seen from FIG. 19, both small (4.7±0.3 mm) and large (8.7±0.5 mm) intact fruitlets (dashed lines) showed an absorption peak at 400-420 nm, probably due to phenolic compounds absorption. Interestingly, the aforementioned feature disappeared after trichome removal (dash-dotted lines), indicating that phenolic compounds were present in fruitlet trichomes. A similar finding for leaf trichomes was previously reported by Solovchenko (2010). Another interesting feature is that the denuded fruitlets of both sizes had almost the same apparent absorption coefficient at 670-675 nm. Since chlorophyll absorption at 670-675 nm did not appear to be saturated, this indicates that the chlorophyll content (per area) of the denuded fruitlets of both sizes was similar. As expected, compared to intact fruitlets, denuded fruitlets had a much higher apparent absorption coefficient in the whole spectral range, with the apparent absorption coefficient of small intact fruitlets being the lowest due to strong trichome scattering. The apparent absorption coefficients of denuded and intact fruitlets all peaked in the blue (440-500 nm) and red (660-680 nm) spectral ranges due to the chlorophyll absorption (carotenoids affect the blue range as well, however in the presence of relatively high chlorophyll content, this effect is less pronounced—(Gitelson & Merzlyak, 2004)). Comparing the apparent absorption coefficients of denuded and intact fruitlets (FIG. 9, dash-dotted vs. dashed lines), it is clear that the difference between them is maximal in the blue and red ranges (FIG. 9, solid lines).

It is worth noting that contrary to big mature apples, which have significant chlorophyll content only in their skin, fruitlets also have a significant chlorophyll concentration in their pulp, which is greenish (supported by destructive chlorophyll analysis, not shown). Multiple scattering from fruitlet trichomes results in random illumination angles (diffuse light), which in turn affects the light path and light penetration depth into the tissue. Brodersen and Vogelmann (2010) for example showed that in leaves light penetration profiles obtained under direct and diffuse light were different.

The effect of trichome density intuitively helps understand the results of the ROC curves for fruitlet classification. The NIR (860-983 nm) range was valuable for fruitlet classification at the earlier monitoring dates (4-6 DAT) for both single-band thresholding (FIG. 14*a*) and band difference thresholding together with the visible range at 400-420 nm (Table 1a). We hypothesise that differences in pigment absorption between dropping and retaining fruitlets were less pronounced at the corresponding dates, and NIR radiation which reflects differences in scattering was preferable for classification. The visible range at 400-420 nm was affected by the absorption of phenolic compounds in fruitlet trichomes (Solovchenko, 2010), and was therefore selected as the second spectral range for band difference thresholding.

The blue (475-493 nm) and red (665-693 nm) were more valuable for fruitlet classification at the later monitoring dates (7-12 DAT) for both band ratio (Table 2a) and single-band thresholding (FIG. 14, panel a). The red-edge (702-720 nm) spectral range was additionally picked in the band ratio thresholding (Table 2a). The differences in fruitlet growth between dropping and retaining fruitlets became more pronounced at 7-12 DAT. The decrease in trichome density in the retaining fruitlets resulted in the reflectance decrease in the whole Vis-NIR spectrum due to much lower trichome scattering. Higher numbers of photons reached the fruitlet surface and sub-surface, which were strongly absorbed in the blue and red spectral ranges by the skin and flesh chlorophyll. Therefore, wavebands near 480 nm and 674 nm strongly related to chlorophyll absorption (Sims & Gamon, 2002; Gitelson & Merzlyak, 2004) were the best bands for fruitlet classification at the later monitoring dates (7-12 DAT). The best ratios (Table 2a) compared reflectance near or at the red-edge (693-720 nm) with the reflectance in the blue or red range (475-493 nm or 665-693 nm), all of which were affected by chlorophyll absorbance, but to a different extent (FIG. 9).

The present study focused on the identification of the most informative Vis-NIR wavelengths for forecasting fruitlet drop. Single-band thresholding highlighted the importance of the NIR spectral region for fruitlet classification at 4-6 DAT, and the blue and red spectral regions at 7-12 DAT. Suitable band differences and band ratios were identified using the ROC curve. We found that at the early stage of fruitlet development (4-6 DAT), applying thresholding to the band difference $R_{973}-R_{404}$ was preferable, while applying thresholding to the band ratio $R_{693}/R_{674}$ was preferable at 7-12 DAT. The selections achieved via the ROC curve were supported by an additional experiment that showed how by itself trichome density affects the reflectance of small and larger fruitlets and modifies pigment absorption.

Compared to our recent results in fruitlet classification based of the whole Vis-NIR range (Orlova et al., 2020), using only two bands (404 nm and 973 nm at 4-6 DAT; 674 nm and 693 nm on later dates) led to slightly lower accuracies (76-95% vs. 80-97% at 6-12 DAT, the use of two to four discrete wavelengths for predicting the chemically-amplified fruitlet drop seems feasible, and the present study could constitute the first step toward the development of a simplified LEDs-based device for the task. Although the full width at half maximum (FWHM) of LEDs in the visible range is ~15 nm, meaning that LEDs centered at 674 nm and 693 nm may overlap, such overlap could be avoided by using optical filters so that there is no major obstacle to such an implementation. Preliminary tests with a prototype under development in our laboratory have shown very promising results that demonstrate the feasibility of this approach. Such a device could be used to scan a large number of fruitlets in-situ, rapidly and non-destructively, paving the way to the more efficient management of chemical thinner applications in particular, and orchard operation in general.

a. As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The invention claimed is:

1. A system comprising:
    at least one hardware processor; and
    a non-transitory computer-readable storage medium having stored thereon program instructions, the program instructions executable by the at least one hardware processor to:
        receive spectral data acquired from a plurality of fruits, wherein said spectral data is obtained within a specified range of wavelengths,
        at a training stage, train a machine learning model on a training set comprising:
        (i) said spectral data, and
        (ii) labels indicating, with respect to each of said fruits, a drop status within a specified time period subsequent to said acquiring, and
        at an inference stage, apply said machine learning model to target spectral data acquired from a target fruit, to predict said drop status of said target fruit within a specified time range subsequent to said acquiring.

2. The system of claim 1, wherein each of said fruits is a fruitlet.

3. The system of claim 1, wherein said specified range of wavelengths is from 400 nm to 1000 nm.

4. The system of claim 1, wherein said spectral data comprises at least one of spectral reflectance data and spectral fluorescence data.

5. The system of claim 1, wherein said spectral data comprises spectral data in one or more specified wavelengths within said specified range of wavelengths.

6. The system of claim 1, wherein said spectral data comprises at least one of: a difference between a pair of specified wavelengths within said specified range of wavelengths, and a ratio between a pair of specified wavelengths within said specified range of wavelengths.

7. The system of claim 1, wherein said acquiring comprises acquiring at least some of said spectral data between 4-16 days after treatment (DAT) of said fruits and said target fruit with a thinning agent.

8. The system of claim 1, wherein said specified time period is between 20-30 DAT of said fruits and said target fruit with a thinning agent.

9. The system of claim 1, wherein said receiving further comprises performing a dimensionality reduction step with respect to said spectral data.

10. The system of claim 1, wherein said receiving further comprises at least one of:
    correcting said spectral data for sunlight contribution during said acquiring, and correcting said spectral data for temperature differences in said fruits during said acquiring.

11. A method comprising:
    receiving spectral data acquired from a plurality of fruits, wherein said spectral data is obtained within a specified range of wavelengths;
    at a training stage, training a machine learning model on a training set comprising:
    (i) said spectral data, and
    (ii) labels indicating, with respect to each of said fruits, a drop status within a specified time period subsequent to said acquiring; and
    at an inference stage, apply said machine learning model to target spectral data acquired from a target fruit, to predict said drop status of said target fruit within a specified time range subsequent to said acquiring.

12. The method of claim 11, wherein each of said fruits is a fruitlet.

13. The method of claim 11, wherein said specified range of wavelengths is from 400 nm to 1000 nm.

14. The method of claim 11, wherein said spectral data comprises spectral data in one or more specified wavelengths within said specified range of wavelengths.

15. The method of claim 11, wherein said spectral data comprises at least one of: a difference between a pair of specified wavelengths within said specified range of wavelengths, and a ratio between a pair of specified wavelengths within said specified range of wavelengths.

16. The method of claim 11, wherein said acquiring comprises acquiring at least some of said spectral data between 4-16 days after treatment (DAT) of said fruits and said target fruit with a thinning agent.

17. The method of claim 11, wherein said specified time period is between 20-30 DAT of said fruits and said target fruit with a thinning agent.

18. The method of claim 11, wherein said receiving further comprises performing a dimensionality reduction step with respect to said spectral data.

19. The method of claim 11, wherein said spectral data comprises at least one of spectral reflectance data and spectral fluorescence data.

20. A computer program product comprising a non-transitory computer-readable storage medium having program instructions embodied therewith, the program instructions executable by at least one hardware processor to:
receive spectral data acquired from a plurality of fruits, wherein said spectral data is obtained within a specified range of wavelengths;
at a training stage, train a machine learning model on a training set comprising:
(i) said spectral data; and
(ii) labels indicating, with respect to each of said fruits, a drop status within a specified time period subsequent to said acquiring, and
at an inference stage, apply said machine learning model to target spectral data acquired from a target fruit, to predict said drop status of said target fruit within a specified time range subsequent to said acquiring.

* * * * *